United States Patent [19]
Isshiki et al.

[11] Patent Number: 5,760,238
[45] Date of Patent: Jun. 2, 1998

[54] 1,4-DIHYDROPYRIDINE DERIVATIVES

[75] Inventors: Kunio Isshiki, Chigasaki; Naoki Matsumoto; Takashi Nakashima, both of Yokohama; Kazuyuki Dobashi, Hadano; Takurou Tsuruta, Iwata; Takeo Yoshioka, Ayase, all of Japan

[73] Assignee: Mercian Corporation, Tokyo, Japan

[21] Appl. No.: 793,283

[22] PCT Filed: Aug. 11, 1995

[86] PCT No.: PCT/JP95/01606

§ 371 Date: Feb. 25, 1997

§ 102(e) Date: Feb. 25, 1997

[87] PCT Pub. No.: WO96/06829

PCT Pub. Date: Mar. 7, 1996

[30] Foreign Application Priority Data

Aug. 29, 1994 [JP] Japan ................................ 6-227227

[51] Int. Cl.$^6$ .................. C07D 211/90; C12P 17/12
[52] U.S. Cl. ................................. 546/321; 435/122
[58] Field of Search ........................ 546/321; 435/122

[56] References Cited

U.S. PATENT DOCUMENTS 5,635,395  6/1997  Isshiki et al. .

OTHER PUBLICATIONS

Holdgrün et al., "A Chemoenzymatic Synthesis of Optically-Active Dihydropyridines" *Tetrahedron Letters*, vol. 32, No. 29, pp. 3465–3468 (1991).

Ebiike et al., "Acyloxymethyl as an Activating Group in Lipase-Catalyzed Enantioselective Hydrolysis . . ." *Tetrahedron Letters*, vol. 32, No. 41 pp. 5805–5808.

Ashimori et al., "Synthesis and Pharmacological Effects of Optically Active . . ." *Chem. Pharm. Bull.*, vol. 39, No. 1, pp. 108–111 (1991).

Ashimori et al., "Novel 1,4–Dihydropyridine Calcium Antagonists . . ." *Chem. Pharm. Bull.*, vol. 39, No. 1, pp. 91–99 (1991).

Tamazawa et al., "Stereoselectivity of a Potent Calcium Antagonist . . ." *J. Med. Chem.*, vol. 29, No. 12, pp. 2504–2511 (1986).

Shibanuma et al., "Synthesis of Optically Active . . ." *Chem. Pharm. Bull.*, vol. 28, No. 9, pp. 2809–2812 (1980).

*Primary Examiner*—Bernard Dentz
*Attorney, Agent, or Firm*—Joseph C. Mason, Jr.

[57] ABSTRACT

Disclosed are 1,4-dihydropyridine derivatives represented by the general formula (I) and salts thereof, as well as optical active 1,4-dihydropyridine derivatives represented by the general formula (II) and salts thereof which are obtained from the derivative by biochemical reactions using microorganisms or enzymes and useful as preventive and therapeutic agents for ischemic heart diseases and hypertension.

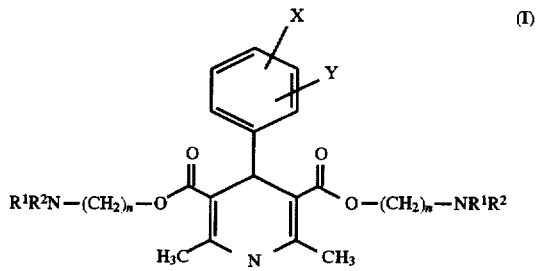

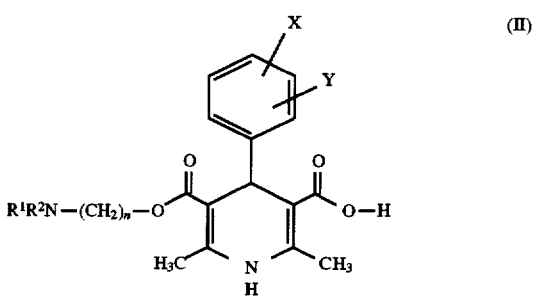

(wherein x and Y are H, $NO_2$, CN, halogen; $R^1$ and $R^2$ are H, CHO, substituted alkylcarbonyl, crotonyl, cinnamoyl, alkoxycarbonyl, aryloxycarbonyl, benzyloxycarbonyl, carboxybenzoyl, or $R^1$ and $R^2$ taken together represent phthaloyl; n is an integer of 1 to 3).

3 Claims, No Drawings

5,760,238

1,4-DIHYDROPYRIDINE DERIVATIVES

This application is a 371 of PCT/JP95/01606 filed Aug. 11, 1995.

TECHNICAL FIELD

The present invention relates to intermediates for preparing optical active 1,4-dihydropyridine derivatives useful as preventive and therapeutic agents for ischemic heart diseases and hypertension. More particularly, the present invention relates to novel 1,4-dihydropyridine derivatives represented by the general formula (I) below

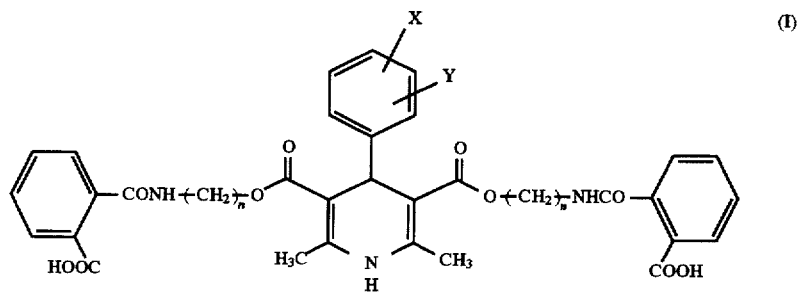

(I)

(wherein the symbols have the same meanings as defined below) and salts thereof, which are substrates for preparing optical active 1,4-dihydropyridine derivatives by biochemical reactions by using microorganisms and enzymes as well as intermediates of the substrates, and to novel optical active 1,4-dihydropyridine derivatives represented by the general formula (II)

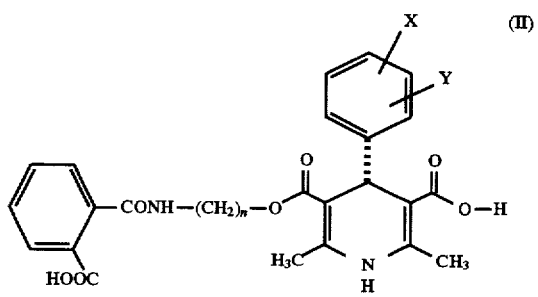

(II)

(wherein the symbols have the same meanings as defined below) and salts thereof.

BACKGROUND ART

Those 1,4-dihydropyridine compounds having two different carboxylic acid ester groups at the 3- and 5-positions, respectively, of the dihydropyridine ring have an asymmetric carbon atom at the 4-position of the dihydropyridine ring and, hence, provide two kinds of optical isomers. Recent research on the biological effects of these compounds has reported that there are differences between the optical isomers in pharmacological activity, in vivo kinetics, safety and so on [K. Tamazawa et al., J. Med. Chem., Vol. 29, 2504 (1986)].

When the compounds having an asymmetric carbon atom are used as a drug, the idea of administering only one of the isomers that is more preferrable as a drug is becoming generally accepted in order not to give an unnecessary load to the living organism. From this viewpoint, investigation has been made for various methods for preparing optical active 1,4-dihydropyridine derivatives.

Generally known methods for synthesizing optical acitve 1,4-dihydropyridine derivatives include the method using (4R)-1,4-dihydropyridinecarboxylic acid monoester as an intermediate, into which a desired ester radical is introduced [A. Ashimori et al., Chem. Pharm. Bull., Vol. 39, 18 (1991)].

As the method for preparing the optical active intermediates, (4R)-1,4-dihydropyridine-3,5-dicarboxylic acid monoesters, there are known the chemical mehtod by Shibanuma et al. [Chem. Pharm. Bull. Vol. 28, 2809 (1980)] and the enzymatic methods by Achiwa et al. [Tetrahedron Letter, 32, 5805 (1991)] and by Charles J. Sih et al. [Tetrahedron Letter, 32, 3465 (1991)].

Among these methods, the enzymatic methods are excellent manufacturing methods since they asymmetrically hydrolyze prochiral 1,4-dihydropyridine-3,5-dicarboxylic acid diesters so that the other of the isomers, that is unusable and wasted in the chemical method, does not have to be wasted.

However, the enzymatic methods require that the reaction should proceed in an aqueous medium due to their nature. Therefore, the conventional methods, in which highly hydrophobic 1,4-dihydropyridine-3,5-dicarboxylic acid diester is used as a substrate, have failed to proceed the reaction at increased substrate concentrations in spite of use of an auxiliary solvent (acetone, methanol, dimethyl sulfoxide, diemthylformamide and so on) so that only a limited reaction efficiency has been obtained.

Accordingly, there has been a keen demand for the development of an efficient method for preparing an optical active isomer, i.e., (4R)-1,4-dihydropyridine-3,5-dicarboxylic acid monoester, using a substrate which has high polarity and is water-soluble.

DISCLOSURE OF THE INVENTION

As a result of intensive investigation with a view to solving the above-described problems, the present inventors have discovered highly water-soluble substrates suitable for preparing (4R)-1,4-dihydropyridine-3,5-dicarboxylic acid monoester derivatives by using microorganisms or enzymes, and thus completed the present invention.

Therefore, the present invention provides 1,4-dihydropyridine derivatives described below.

1) 1,4-dihydropyridine derivatives represented by the general formula (I)

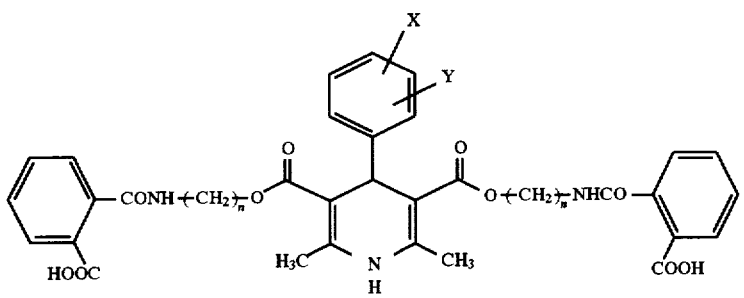

(I)

(wherein X and Y independently represent a hydrogen atom, a nitro group, a nitrile group or a halogen atom, and n is an integer of 1 to 3) or salts thereof.

2) Optical active 1,4-dihydropyridine derivatives represented by the general formula (II)

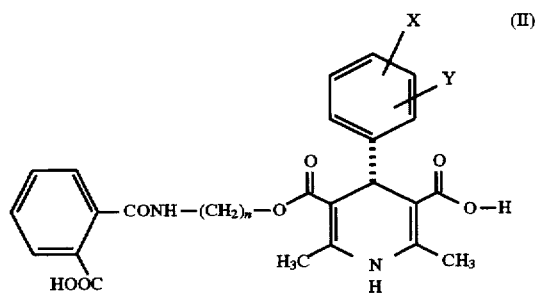

(II)

(wherein X, Y and n have the same meanings as defined above) or salts thereof.

3) A method for preparing an optical active 1,4-dihydropyridine derivative represented by the general formula (II)

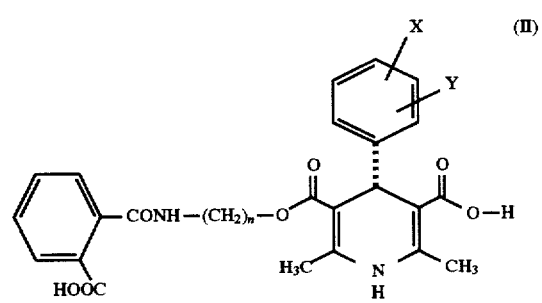

(II)

(wherein X, Y and n have the same meanings as defined above) or salts thereof, comprising the step of subjecting a 1,4-dihydropyridine derivative represented by the general formula (I)

(wherein X, Y and n have the same meanings as defined above) or salts thereof to asymmetric hydrolysis using a microorganism or enzyme.

The 1,4-dihydropyridine derivatives represented by the general formula (I) above and salts thereof have high solubilities in water and serve a novel substrate useful for preparing optical active 1,4-dihydropyridine derivatives by biochemical reactions using a microorganism or enzyme.

The optical active 1,4-dihydropyridine derivatives represented by the general formula (II) and salts thereof are novel optical active 1,4-dihydropyridine derivative, which can be obtained from the compounds represented by the general formula (I) above by biochemical reactions and are intermediates for preparing compounds useful as preventive and therapeutic drugs for ischemic heart diseases or hypertension.

In the compounds represented by the general formula (I) or (II), the positions at which substituents X and Y (nitro, group, nitrile group or halgen atom) on the phenyl group attached to the 4-position of the pyridine ring are not limited particicularly but may be either one of the 2-,3- and 4-positions.

The halogen atoms represented by x and Y include a fluorine atom, a chlorine atom, a bromine atom and an iodine atom, with a chlorine atom being preferred.

In the compounds represented by the general formula (I) or (II), the interger of 1 to 3 represented by n is preferably 2 or 3, with 2 being particularly preferred.

[Salts]

The compounds represented by the general formulae (I) and (II) above can be converted to salts by conventional methods. The compounds represented by the general formula (I) are used in the form of free compounds as a substrate for biochemical reactions using microorganisms or enzymes and can be used as a substrate also in the form of salts thereof.

The salts of the compounds represented by the general formulae (I) and (II) include salts of organic acids such as acetic acid, tartaric acid, benzenesulfonic acid, trifluoroacetic acid and the like, salts of inorganic acids such as

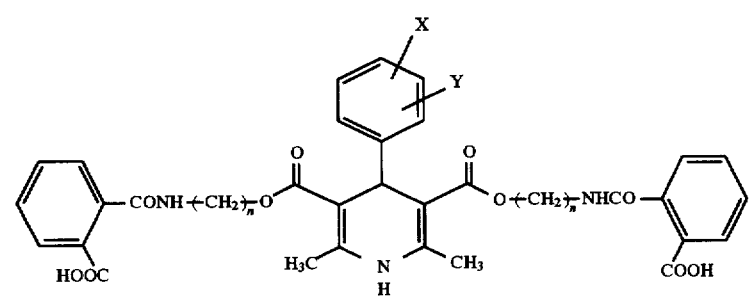

(I)

hydrochloric acid, sulfuric acid and the like, salts of organic bases such as morpholine, triethylamine, triethylenediamine and the like, salts of alkali metals such as sodium, potassium, lithium and the like.

[Method for Preparing Compound (I)]

The compounds represented by the general formula (I) can be prepared by combinations of methods which are known per se.

The compounds represented by the general formula (I) can be prepared, for example, according to Reaction Scheme-1 below.

In the below reaction scheme, $R^1$ and $R^2$ represent a combination of a hydrogen atom and a 2-carboxybenzoyl group, or $R^1$ and $R^2$ taken together represent a phthaloyl group. The other symbols have the same meanings as defined above.

The reaction scheme will be described briefly below.

First, an ethanol amine derivative (III) with its amino group(s) being protected is reacted with a diketene (IV) to give an acetoacetic acid ester derivative (V) (step a). Then, the acetoacetic acid ester derivative (V) and ammonia (VI) are reacted to form a β-aminocrotonic acid ester derivative (VII) (step b). Also, the acetoacetic acid ester derivative (V) and a benzaldehyde derivative (VIII) are condensed to produce an α-benzylidene-β-ketoester derivative (IX) (step c). Next, the β-aminocrotonic acid ester derivative (VII) and the α-benzylidene-β-ketoester derivative (IX) are condensed by heating (step d) to produce the target compound.

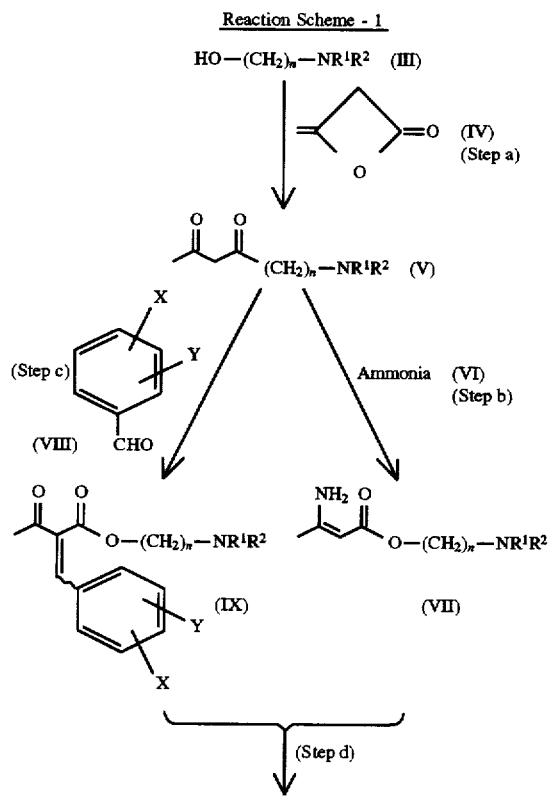

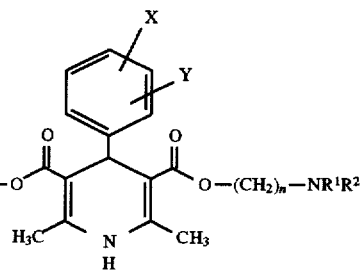

The step a can be performed by dropwise adding a diketene (IV) to a solution of an ethanolamine derivative (III) in an inert solvent (tetrahydrofuran (THF) or the like) in the presence of a base (triethylamine or the like) and stirring the resulting mixture for 1 to 24 hours at a temperature being in the range of from 0° to 100° C.

The step b can be carried out by adding an ammonium salt which is easy to handle (ammonium carbonate or the like) to a solution of acetoacetic ester derivative (V) in an inert solvent (ethanol or the like) and stirring the resulting mixture at 15° to 60° C. for 1 to 24 hours.

The step c can be performed by adding the benzaldehyde derivative (VIII) to a solution of the acetoacetic acid ester derivative (V) in an inert solvent (dioxane or the like) and heating the resulting mixture at 80° to 110° C. for 2 to 24 hours with stirring.

The step d can be peformed by stirring the β-aminocrotonic acid ester (VII) and the α-benzylidene-β-ketoester derivative (IX) at 50° to 90° C. for 2 to 24 hours in the presence or absence of inert solvents (dioxane or the like).

Also, the steps b, c and d can be performed at a time. That is, the target compound can be produced in one step by heat-condensing 2 equivalents of acetoacetic ester derivative (V) with ammonia (VI) and benzaldehyde derivative (VIII) (Reaction Scheme-2).

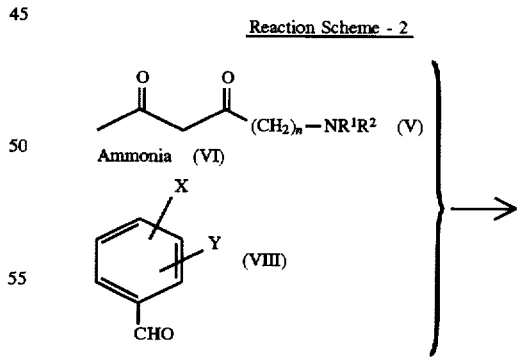

Also, the target compounds can be prepared by the method in which the acetoacetic ester derivative (V), β-aminocrotonic acid ester derivative (VII), and the benzaldehyde derivative (VIII) are heat-condensed (Reaction Scheme-3), or by the method in which the acetoacetic acid ester derivative (V), the α-benzylidene-β-ketoester derivative (IX), and the ammonia (VI) are heate-condensed (Reaction Scheme-4).

Reaction Scheme - 3

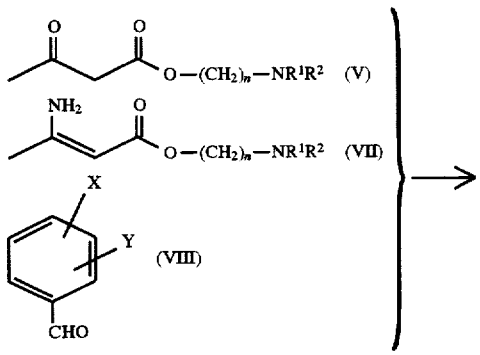

Reaction Scheme - 4

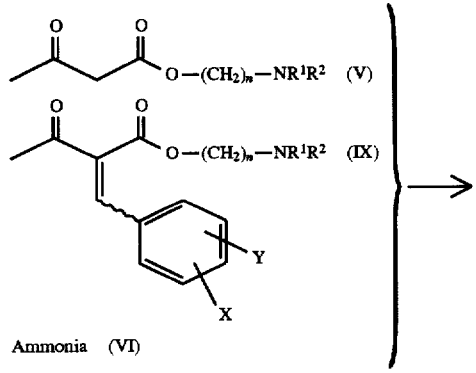

Among the compounds obtained as described above, the compounds (Ia) in which $R^1$ and $R^2$ taken together represent a phthaloyl group can be converted to the compounds represented by the general formula (I) by subjecting the compounds to a hydrolysis reaction.

[Metod for Preparing Comound (II)]

The optical active 1,4-dihydropyridine compounds represented by the general formula (II) can be prepared by an asymmetric hydrolysis reaction of the compounds using a microorganism or enzyme represented by the general formula (I).

The microorganisms which can be used in the reaction include those microorganisms which belong to the genera Streptomyces, Paecilomyces, Botryodioplodia, Altenaria or Helminthosporium and have capabilities of asymmetric hydrolysis. Examples of such microorganisms include FI-4 strain, FI-741 strain, FI-1007 strain and A-914 strain. The morphological properties of these fungi will be described below.

FI-4 Strain

This strain forms pale greyish white cotton-like mycelia on a potato dextrose agar medium, the base of the mycelia becoming blackish grey with a progress of cultivation. The conidia are of poro-type that grow through small holes at the apex of the conidiophore and separated by septa to have a shape of stacked bricks. The bottom of the conidia is round with the pointed apex, and the color is brown.

FI-741 Strain

This strain forms well developed white cotton-like mycelia on a potato dextrose agar medium, the base of the mycelia becoming brown with a progress of cultivation. The conidia are formed in a spherical organ called pycnidium having an opening in the apex. The conidia are relatively long, smooth and not viscous. Upon maturity, they turn brown and have thickened cell walls.

FI-1007 Strain

This strain forms greyish white mycelia on a potato dextrose agar medium, the base of the mycelia becoming slightly pinkish brown with a progress of cultivation. The conidia are of a phialo-type that emerge from the topmost phialide on a conidiophore. The conidiophore mostly does not form forks but the phialide forks often to take an oblong configuration.

Search was made based on the morphological properties described above consulting with The General of Fungi

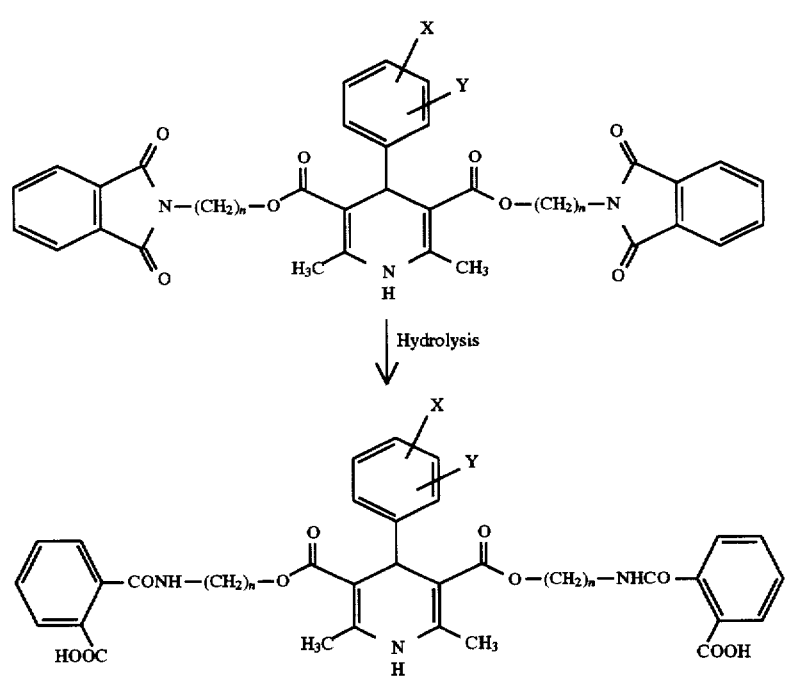

Sporulating in Pure Culture (J. A. von ARX (1970)), which resulted in the identification of FI-4 strain as Alternaria sp., FI-741 as Botryodioplodia sp., FI-1007 as Paecilomyces sp. A-914 Strain This strain forms a pale brown solid colony on an ISP-2 agar medium. With a progress of cultivation, the surface of the colony turns pale greyish green. It produces no melanine pigment or no other dispersive pigment. The hyphae in the medium develop well without being cut and there are aerial hyphae. On the aerial hyphae are coadunating many conidia which are spirally chained. The surface of the conidia is smooth. The cell wall contains L-diaminopimelic acid. It does not assimilate L-hydroxyproline. It is sensitive to 100μg/ml of oleandomycin. Search was made based on the morphological properties described above consulting with Bergey's Mannual of Systematic Bacteriology Volume 4, which resulted in the identification of A-914 as *Streptomyces viridosporus*.

FI-4 strain was deposited at National Institute of Bioscience and Human-Technology, Agency of Industrial Science and Technology under the accession number of FERM P-13535. Thereafter, the deposit was transferred to a deposit under Budapest Treaty on Jun. 14, 1993 and given the accession number of FERM BP-4335.

FI-741 strain, FI-1007 strain, and A-914 strain were deposited at National Institute of Bioscience and Human-Technology, Agency of Industrial Science and Technology on Jul. 29, 1992 under the accession number of FERM P-13097, FERM P-13096, and FERM P-13098, respectively. Thereafter, the deposits were transferred to deposits under Budapest Treaty on Jun. 14, 1993 and given the accession numbers of FERM BP-4333, FERM BP-4332, and FERM BP-4334, respectively.

The microorganisms which can be used in the present invention include Streptomyces sp. ATCC11862 and Helminthosporium zonatum IFO 6678. These microorganisms were deposited at the American Type Culture Collection and Institute For Fermentation, OSAKA, respectively, and are available with ease.

Cultivation media for cultivating the above-described microorganisms are not particularly limited but any medium to be employed for cultivating ordinary microorganisms can be used.

For example, as a carbon source, there can be used any substance that the above-described microorganisms assimilate. More specifically, there can be used sugar such as glucose, fructose, sucrose, dextrines and the like; sugar alcohols such as glycerol, sorbitol and the like; and organic acids such as fumaric acid, succinic acid and the like. The amount of carbon sources which are added to the medium is preferably in amounts of usually about 0.1 to 10% by weight.

As a nitrogen source, there can be used, for example, inorganic ammonium salts such as ammonium chloride, ammonium sulfate, ammonium phosphate and the like; ammonium salts of organic acids such as ammonium fumarate, ammonium succinate and the like; natural organic nitrogen sources such as meat extracts, yeast extracts, corn steep liquor, casein hydrolysates and the like, and so on. Among them, the organic nitrogen sources can be used as a carbon source as well. Suitable amount of the nitrogen source is usually from 0.1 to 10% by weight.

As inorganic salts, there can be used, for example, alkali metal phosphates such as potassium phosphate, sodium phosphate and the like; alkali metal chlorides such as potassium chloride, sodium chloride and the like; metal sulfates such as magnesium sulfate, ferrous sulfate and the like, and so on. Suitable amount thereof is from 0.001 to 1% by weight.

The microorganisms may be cultivated in the above-described medium at 20° to 40° C., preferably from 28° to 37° C. at a pH of 5 to 9, preferably 6 to 8 under aerobic conditions.

The reaction in which a microorganism is used can be performed by a reaction of the microorganism or processed product thereof with the compound represented by the general formula (I). The reaction with a microorganism usually is a reaction with an enzyme contained in the culture of the microorganism.

As the culture of a microorganism, there can be used any of the cells of the cultivated microorganism, filtrate of the culture, and culture liquor.

The processed product of a microorganism means a processed product of the cells of the microorganism, which includes dry cells, for example, lyophylized cells, spray-dried cells, or cells treated with an organic solvent, for example, acetone, toluene, methanol, butanol or the like, cell extracts, and insolubilization products. The processed products of culture filtrate and culture liquor include concentrates, dried powder, and spray-dried powder of culture liquor.

Further, enzymes isolated from the cultivated cells and culture filtrate and purified may be reacted with the above-described processed products of the raw material.

In practicing the present invention, a culture liquor containing $10^6$ to $10^{10}$ cells/ml of a microorganism can be obtained by inoculating the microorganism in a culture medium and cultivating it at 20° to 40° C. for 12 to 120 hours. To the culture liquor is added an aqueous solution of the compound represented by the general formula (I) in a final concentration of usually 0.5 to 5 mg/ml, followed by reaction usually at 28° C. for 18 to 72 hours. Then, the reaction mixture is adjusted to pH 5 and extracted with an organic solvent such as chloroform, ethyl acetate, butyl acetate, butanol or the like, followed by crystallization, solvent extraction, precipitation or the like to obtain the target optical active compound represented by the general formula (II).

The enzymes which can be used in the reaction include protease, protease P-6 (Amano Pharmaceutical Co., Ltd.), for instance, and the like. In practicing the present invention using the enzyme, a material compound represented by the general formula (I) is added to a buffer solution adjusted to pH5~10 in a final concentration of usually 1 to 100 mg/ml. To the mixture is added the enzyme to dissolve, followed by reaction at 25° to 40° C. for 6 to 48 hours. The reaction mixture is then extracted with an organic solvent in the same manner of the reaction using microorganism cells, such as crystallization, solvent extraction, precipitation or the like, to obtain the target optical active compound represented by the general formula (II).

[Preferred Compounds]

Among the compounds represented by the general formula (I), preferred compounds which can be used as a substrate for biochemical reactions to obtain optical active 1,4-dihydropyridine derivatives represented by the general fromula (II) include (1) 1,4-dihydro-2,6-dimethyl-4-(3-nitrophenyl)pyridine-3, 5-dicarboxylic acid bis[2-(2-carboxybenzoyl)aminoethyl] ester,.

(2) 1,4-dihydro-2,6-dimethyl-4-(2-chlorophenyl)pyridine-3, 5-dicarboxylic acid bis[2-(2-carboxybenzoyl)aminoethyl] ester, (3) 1,4-dihydro-2,6-dimethyl-4-(3-chlorophenyl)pyridine-3, 5-dicarboxylic acid bis[2-(2-carboxybenzoyl)aminoethyl] ester, (4) 1,4-dihydro-2,6-dimethyl-4-(2,3-dichlorophenyl) pyridine-3,5-dicarboxylic acid bis[2-(2-carboxybenzoyl) aminoethyl] ester, (5) 1,4-dihydro-2,6-dimethyl-4-(2-fluorophenyl)pyridine-3, 5-dicarboxylic acid bis[2-(2-carboxybenzoyl)aminoethyl] ester, (6) 1,4-dihydro-2,6-dimethyl-4-(3-fluorophenyl)pyridine-3, 5-dicarboxylic acid bis[2-(2-carboxybenzoyl)aminoethyl] ester, (7) 1,4-dihydro-2,6-dimethyl-4-(3-cyanophenyl)pyridine-3, 5-dicarboxylic acid bis[2-(2-carboxybenzoyl)aminoethyl] ester, (8) 1,4-dihydro-2,6-dimethyl-4-(2-nitrophenyl)pyridine-3, 5-dicarboxylic acid bis[2-(2-carboxybenzoyl)aminoethyl] ester, (9) 1,4-dihydro-2,6-dimethyl-4-(3-nitrophenyl)pyridine-3, 5-dicarboxylic acid bis[3-(2-carboxybenzoyl) aminopropyl] ester,

(10) 1,4-dihydro-2,6-dimethyl-4-(3-nitrophenyl) pyridine-3, 5-dicarboxylic acid bis (2-carboxybenzoylaminomethyl) ester, and salts thereof.

Preferred optical active 1,4-dihydropyridine derivatives represented by the general formula (II) include

(11) (4R)-1,4-dihydro-2,6-dimethyl-3-[2-(2-carboxybenzoyl) aminoethyl]oxycarbonyl-4-(3-nitrophenyl) pyridine-5-carboxylic acid,

(12) (4R)-1,4-dihydro-2,6-dimethyl-3-[2-(2-carboxybenzoyl) aminoethyl]oxycarbonyl-4-(2,3-dichlorophenyl) pyridine-5-carboxylic acid,

(13) (4R)-1,4-dihydro-2,6-dimethyl-3-[2-(2-carboxybenzoyl)aminoethyl]oxycarbonyl-4-(3-chlorophenyl)pyridine-5-carboxylic acid,

(14) (4R)-1,4-dihydro-2,6-dimethyl-3-[2-(2-carboxybenzoyl)aminoethyl]oxycarbonyl-4-(3-cyanophenyl)pyridine-5-carboxylic acid,

(15) (4R)-,4-dihydro-2,6-dimethyl-3-[3-(2-carboxybenzoyl) aminopropyl]oxycarbonyl-4-(3-nitrophenyl)pyridine-5-carboxylic acid,

(16) (4R)-1,4-dihydro-2,6-dimethyl-3-[(2-carboxybenzoyl) aminomethyl]oxycarbonyl-4-(3-nitrophenyl)pyridine-5-carboxylic acid, and so on.

INDUSTRIAL APPLICABILITY

The 1,4-dihydropyridine derivatives represented by the general formula (I), and the 1,4-dihydropyridine derivatives represented by the general formula (II) above as well as salts thereof have higher solubility in water than prochiral 1,4-dihydropyridine-3,5-dicarboxylic acid diester used as a substrate for the conventional asymmetric hydrolysis by several hundreds to several ten thousands times, and, hence, are very useful as a substrate for preparing optical active 1,4-dihydropyridine derivatives by biochemical reactions using microorganisms or enzymes.

Also the 1,4-dihydropyridine derivatives represented by the general formula (I) above are useful as a raw material for preparing the compounds represented by the general formula (II).

Further, the novel optical active 1,4-dihydropyridine derivatives represented by the general formula (II) and salts thereof obtained from the compounds represented by the general formula (I) above by biochemical reactions are intermediates for preparing compounds useful as preventive and therapeutic drugs for ischemic heart diseases or hypertension.

That is, the novel compounds represented by the general formulae (I) and (II) above can be used preferably as an intermediate for preparing, for example, (4R)-(2-nicotinoylamino)ethyl(3-nitrooxy) propyl-1,4-dihydro-2,6-dimethyl-4-(3-nitrophenyl)pyridine-3,5-dicarboxylate (Extended Print of the 112th Anniversary of Japan Pharmaceutical Association, Drug Section 30ZF 11–2, page 245, and JP-A-2-223580 publication), (4S)-2,6 dimethyl-(3-nitrophenyl)-1,4-dihydropyridine-3,5-dicarboxylic acid(3S) -3-(1-benzyl-3-pyrolidyl)ester methyl ester [J. Med. Chem., 29, 2504 (1988)], and (4S)-2,6-dimethyl-(3-nitrophenyl)-1, 4-dihydropyridine-3,5-dicarboxylic acid 3-{2-[4-(4-benzhydryl-3-piperazinyl)phenyl]ethyl}ester methyl ester [Chem. Pharm. Bull., 39, 108 (1991)] and, hence, are highly useful.

BEST MODE FOR CARRYING OUT THE INVENTION

Hereafter, the present invention will be described by reference examples, examples, and test examples. However, the present invention should not be construed as being limited to the following examples. Unless otherwise indicated specifically, % represents % by weight. As the absorbent for TLC was used silica gel (Art 5715 manufactured by Merck, Inc.).

Reference Example 1

Preparation of 1,4-dihydro-2,6-dimethyl-4-(3-nitrophenyl) pyridine-3,5-dicarboxylic acid bis(2-acetamidoethyl) ester

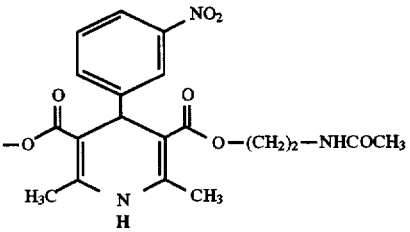

To a solution of 25 g of N-acetylethanolamine in 100 ml of dioxane was added 0.34 ml of triethylamine and 18.7 ml of diketene was slowly dripped to the resulting mixture. After the exothermic reaction was over, 8.1 ml of concentrated ammonia water and 18.3 g of m-nitrobenzaldehyde were added and the resulting mixture was heated and stirred in an oil bath at 80° C. for 17 hours. The solvent was distilled off under reduced pressure, and the residue obtained was purified through a column filled with 700 g of silica gel with a toluene/acetone mixed solvent (mixing ratio 2:1) as a developer to obtain 24 g of the target compound. H-NMR (CDCl$_3$): δ 8 8.23 (1 H,t,J=2 Hz), 8.00(1 H,td,J=1 Hz, 2 Hz, 8 Hz), 7.70(1 H,td,J=1 Hz,2 Hz,8 Hz), 7.40(1 H,t,J=8 Hz), 6.85(2 H,t,J=6 Hz), 6.67(1 H,s), 5.11(1 H,S), 4.20(2 H,m), 3.95(2 H,m), 3.60(2 H,m), 3.48(2 H,m), 2.36(6 H,s), 1.98(6 H,s); FAB-MS(m/z): 489(M+H)$^+$

Reference Example 2

Preparation of 1,4-dihydro-2,6-dimethyl-4-(3-nitrophenyl) pyridine-3,5-dicarboxylic acid bis(2-aminoethyl) ester

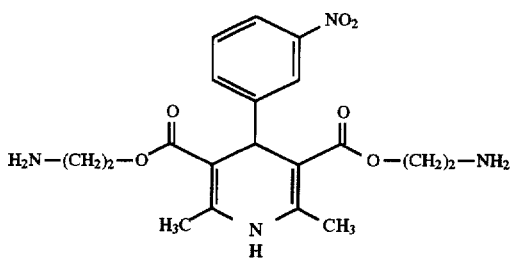

100 mg of the 1,4-dihydro-2,6-dimethyl-4-(3-nitrophenyl)pyridine-3,5-dicarboxylic acid bis(2-acetamidoethyl) ester prepared in Reference Example 1 was suspended in a mixed solvent cosisting of 1 ml of tetrahydrofuran and 1 ml of 1N hydrochloric acid solution and the suspension was heated and stirred in an oil bath at 60° C. for 4 hours. After adding 20 ml of water to the reaction mixture and distilling tetrahydrofuran off under reduced pressure, 20 ml of acetic acid was added to the mixture and the mixture was separated. To the aqueous phase was added an aqueous 1N sodium hydroxide solution to adjust the mixture to pH 10 and then 100 ml ethyl acetate was added for separation and extraction. The orgaic phase thus obtained was washed with water, followed by drying over anhydrous sodium sulfate and distilling the solvent off under reduced pressure to obtain 32 mg of the target compound.

TLC: Rf 0.18 (butanol : acetic acid : water=4:1:2); $^1$H-NMR(D$_2$O-DCl):δ 8.17(1 H,s), 8.10 (1H,d,J=8 Hz), 7.80(1 H,d,J=8 Hz), 7.56(1 H,t,J=8 Hz), 5.07(1 H,s), 4.5–4.2(4 H,m), 3.36(4 H,br), 2.36(6 H,s) FAB-MS (m/z) =405 (M+H)$^+$glycerol matrix Reference Example 3
Preparation of 1,4-dihydro-2,6-dimethyl-4-(3-nitrophenyl) pyridine-3,5-dicarboxylic acid bis(2-t-butoxycarbonhylaminoethyl) ester

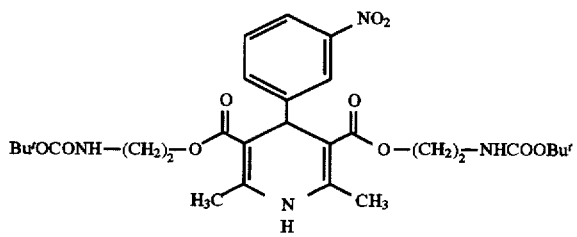

To a solution of 1.875 g of 2-tbutoxycarbonylaminoethanol in 8 ml of tetrahydrofuran were added 0.16 ml of triethylamine and then 0.99 ml of diketene dropwise, followed by stirring at room temperature for 3 hours. The reaction mixture was concentrated under reduced pressure. The crude 2-t-butoxycarbonylaminoethyl acetoacetate thus obtained was dissolved in 10 ml of ethanol and 280 mg of ammonium carbonate was added to the resulting solution, and the mixture was stirred at 45° C. for 2 hours. The reaction mixture was again concentrated under reduced pressure to obtain a mixture of acetoacetic acid ester and β-aminocrotonic acid ester, which mixture was dissolved in 10 ml of dioxane, followed by addition of 879 mg of m-nitrobenzaldehyde. The resulting mixture was heated and stirred at 80° C. for 18 hours. The residue obtained after concentration of the reaction mixture was purified through a column filled with 500 ml of silica gel with a toluene/acetone mixed solution (toluene:acetone=20:1) as a developer to obtain 2.23 g (yield 63%) of the target compound.

TLC: Rf 0.21 (toluene:acetone=5:1) $^1$H-NMR(CDCl$_3$):δ 8.11(1 H,s), 8.02(1 H,d,,J=8 Hz), 7.67(1 H,d,J=8 Hz), 7.42(1 H,t,J=8 Hz), 5.96(1 H,br), 5.08(1 H,s), 4.65(2 H,br), 4.10(4 H,m), 3.5–3.2(4 H,m), 2.37(6 H,s), 1.42(18 H,s)

Reference Example 4
Preparation of 1,4-dihydro-2,6-dimethyl-4-(3-nitrophenyl) pyridine-3,5-dicarboxylic acid bis(2-aminoethyl) ester dihydrochloride

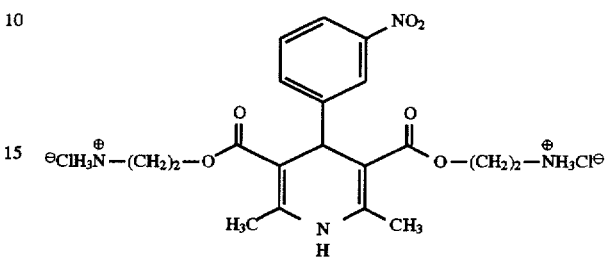

1.996 g of the 1,4-dihydro-2,6-dimethyl-4-(3-nitrophenyl)pyridine-3,5-dicarboxylic acid bis(2-tbutoxycarbonhylaminoethyl) ester prepared in Reference Example 3 was dissolved in 10 ml of chloroform. To the solution was added 13 ml of a hydrochloric acid/dioxane solution (2N) and the resulting mixture was heated and stirred at 40° C. for 4 hours. Insoluble matters which appeared were removed by filtration and washed with 20 ml of hexane and dried to obtain 1.49 g of the target compound as yellow powder.

TLC: Rf 0.18 (butanol:acetic acid:water=4:1:2); $^1$H-NMR (D$_2$O):δ 8.17(1 H,s), 8.10(1 H,d,J=8 Hz), 7.80(1 H,d,J=8 Hz), 7.56(1 H,t,J=8 Hz), 5.07(1 H,s), 4.5–4.2(4 H,m), 3.36(4 H,br), 2.36(6 H,s) FAB-MS(m/z):405 (M+H)$^+$glycerol matrix Reference Example 5
Preparation of 1,4-dihydro-2,6-dimethyl-4-(3-chlorophenyl) pyridine-3,5-dicarboxylic acid bis(2-t-butoxycarbonylaminoethyl) ester

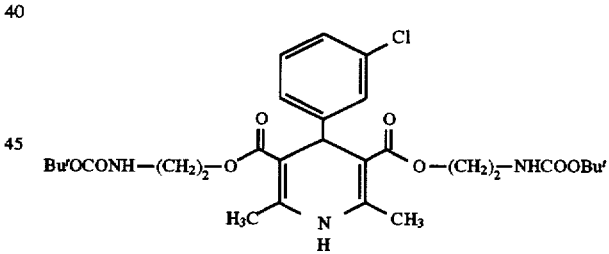

1.00 g of crude 2-t-butoxycarbonylaminoethyl acetoacetate obtained in the same manner as in Reference Example 3 was dissolved in 5 ml of ethanol. After addition of 137 mg of ammonium carbonate, the solution was stirred at 50° C. for 2.5 hours, followed by addition of 0.254 ml of 3-chlorobenzaldehyde and heating at reflux for 3 hours. The residue obtained after distilling the solvent off under reduced pressure was charged in a column filled with 100 g of silica gel and developed with toluene/acetone mixed solvent as a developer (mixing ratio 6:1) for purification to obtain 1.00 g (yield 83%) of the target compound.

TLC: Rf 0.35 (toluene:acetone=4:1); $^1$H-NMR(CDCl$_3$):δ 7.3–7.1(4 H,m), 5.79(1 H,s), 4.93(1 H,bs), 4.58(2 H,bs), 4.2–4.0(4 H,m), 3.5–3.3(4 H,m), 2.35(6 H,s), 1.43(18 H,s); FAB-MS(m/z):594 (M+H)$^+$m-nitrobenzyl alcohol matrix; IR(KBr):3339, 2978, 1692, 1493, 1273, 1213, 1171, 1117 cm$^{-1}$

Reference Example 6

Preparation of 1,4-dihydro-2,6-dimethyl-4-(3-chlorophenyl)pyridine-3,5-dicarboxylic acid bis(2-aminoethyl) ester dihydrochloride

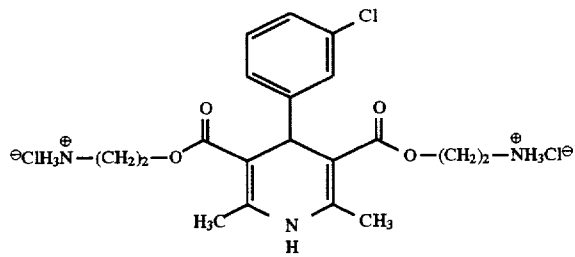

492 mg of the 1,4-dihydro-2,6-dimethyl-4-(3-chlorophenyl)pyridine-3,5-dicarboxylic acid bis(2-tbutoxycarbonylaminoethyl) ester prepared in Reference Example 5 was dissolved in 4 ml of THF. 1 ml of concentrated hydrochloric acid was added to the solution and the mixture was stirred at 50° C. for 2.5 hours. To the residue obtained after distilling the solvent off under reduced pressure was added 2 ml of ethanol, and the mixture was stirred at 0° C. for 10 minutes, filtered, washed with cold ethanol and dried to obtain 139 mg (yield 36%) of the target compound.

TLC: Rf 0.47 (butanol:acetic acid:water=4:1:1) $^1$H-NMR (D$_2$O):δ 7.39(1 H,s), 7.35–7.25(3 H,m), 4.92(1 H,s), 4.42–4.27(4 H,m), 3.35–3.25(4 H,m), 2.33(6 H,s) FAB-MS (m/z): 394(M+H)$^+$glycerol matrix IR(KBr):3246, 2975, 1688, 1483, 1273, 1213, 1115, 1100 cm$^{-1}$

Reference Example 7

Preparation of 1,4-dihydro-2,6-dimethyl-4-(2-chlorophenyl)pyridine-3,5-dicarboxylic acid bis(2-t-butoxycarbonylaminoethyl) ester

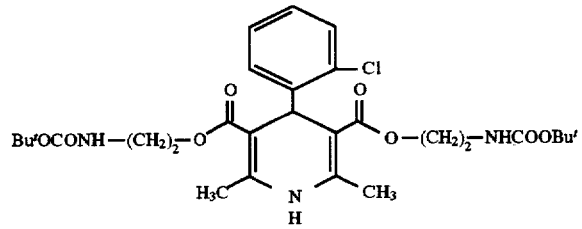

The reaction, treatment and purification procedures of Reference Example 5 were repeated except for using 0.253 ml of 2-chlorobenzaldehyde to obtain 965 mg (yield 80%) of the target compound.

TLC: Rf 0.37 (toluene:acetone=4:1); $^1$H-NMR(CDCl$_3$):δ 7.43–7.39(1 H,m), 7.31–7.23(1 H,m), 7.21–7.16(1 H,m), 7.11–7.06(1 H,m), 5.81(1 H,bs), 5.34(1 H,s), 4.64(2 H,bs), 4.15–4.03(4 H,m), 3.4–3.2(4 H,m), 2.32(6 H,s), 1.44(18 H,s); FAB-MS (m/z):594 (M+H)$^+$m-nitrobenzyl alcohol matrix; IR(KBr): 3347, 2978, 1696, 1497, 1273, 1209, 1171, 1115 cm$^{-1}$

Reference Example 8

Preparation of 1,4-dihydro-2,6-dimethyl-4-(2-chlorophenyl)pyridine-3,5-dicarboxylic acid bis(2-aminoethyl) ester dihydrochloride

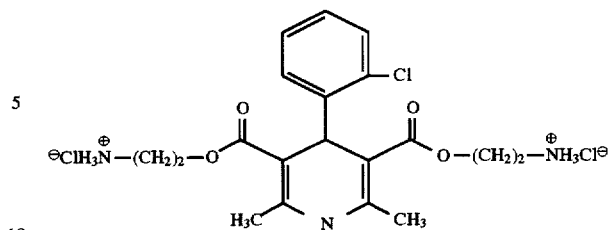

The reaction, treatment and purification procedures of Reference Example 6 were repeated except for using 673 mg of 1,4-dihydro-2,6-dimethyl-4-(2-chlorophenyl)pyridine-3,5-dicarboxylic acid bis(2-t-butoxycarbonylaminoethyl) ester prepared in Reference Example 7 to obtain 426 mg (yield 81%) of the target compound.

TLC: Rf 0.45 (butanol:acetic acid:water=4:1:1); $^1$H-NMR (D$_2$O):δ 7.59–7.56(1 H,m), 7.43–7.39(1 H,m), 7.35–7.30(1 H,m), 7.26–7.20(1 H,m), 5.34(1 H,s), 4.4–4.2(4 H,m), 3.40–3.25(4 H,m), 2.32(6 H,s); FAB-MS(m/z):394 (M+H) $^+$glycerol matrix IR(KBr):3434, 2978, 1698, 1493, 1273, 1209, 1113 cm$^{-1}$

Reference Example 9

Preparation of 1,4-dihydro-2,6-dimethyl-4-(2,3-dichlorophenyl)pyridine-3,5-dicarboxylic acid bis(2-t-butoxycarbonylaminoethyl) ester

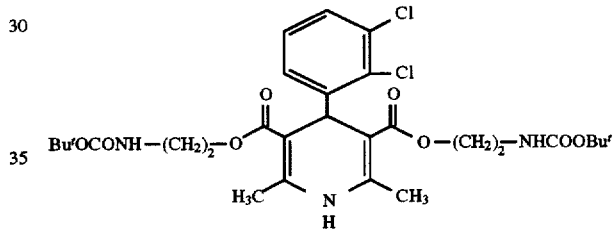

The reaction, treatment and purification procedures of Reference Example 5 were repeated except for using 392 mg of 2,3-dichlorobenzaldehyde to obtain 964 mg (yield 75%) of the target compound.

TLC: Rf 0.43 (toluene:acetone=3:1); $^1$H-NMR(CDCl$_3$):δ 7.35–7.25(2 H,m), 7.15–7.09(1 H,m), 5.83(1 H,bs), 5.42(1 H,s), 4.66(2 H,bs), 4.15–4.05(4 H,m), 3.45–3.25(4 H,m), 2.32(6 H,s), 1.43(18 H,S); FAB-MS (m/z):628 (M+H)$^+$m-nitrobenzyl alcohol matrix IR(KEr):3349, 2978, 1696, 1497, 1275, 1211, 1171, 1115 cm$^{-1}$

Reference Example 10

Preparation of 1,4-dihydro-2,6-dimethyl-4-(2,3-dichlorophenyl)pyridine-3,5-dicarboxylic acid bis(2-aminoethyl) ester dihydrochloride

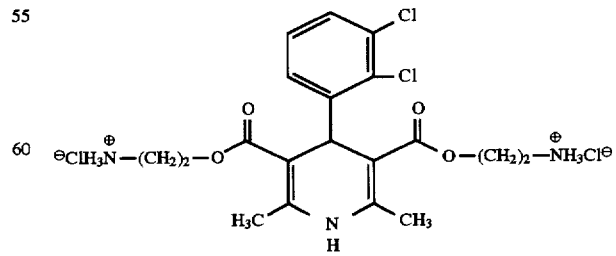

The reaction, treatment and purification procedures of Reference Example 6 were repeated except for using 455 mg of 1,4-dihydro-2,6-dimethyl-4-(2,3-dichlorophenyl) pyridine-3,5-dicarboxylic acid bis(2-t-butoxycarbonylaminoethyl) ester prepared in Reference Example 9 to obtain 223 mg (yield 61%) of the target compound.

TLC: Rf 0.45 (butanol:acetic acid:water=4:1:1); $^1$H-NMR (D$_2$O):δ 7.54–7.48(1 H,m), 7.46–7.41(1 H,m), 7.29–7.24(1 H,m), 5.42(1 H,s), 4.41–4.22(4 H,m), 3.38–3.24(4 H,m), 2.31(6 H,s) FAB-MS(m/z):428 (M+H)$^+$glycerol matrix; IR(KBr)=3432, 2975, 1690, 1489, 1277, 1211, 1113 cm$^{-1}$ Reference Example 11

Preparation of 1,4-dihydro-2,6-dimethyl-4-(3-cyanophenyl) pyridine-3,5-dicarboxylic acid bis(2-t-butoxycarbonylaminoethyl) ester

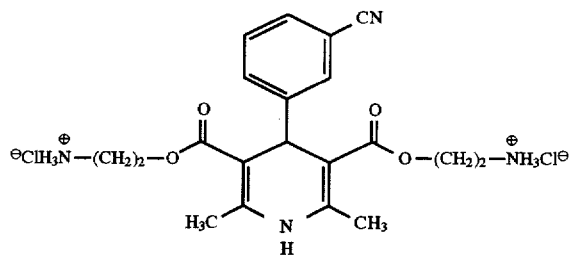

The reaction, treatment and purification procedures of Reference Example 6 were repeated except for using 422 mg of 1,4-dihydro-2,6-dimethyl-4-(3-cyanoophenyl)pyridine-3,

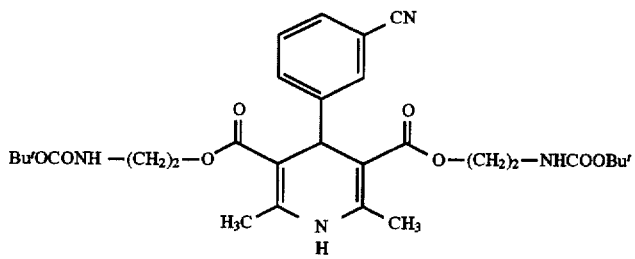

The reaction, treatment and purification procedures of Reference Example 5 were repeated except for using 300 mg of 3-cyanobenzaldehyde to obtain 900 mg (yield 76%) of the target compound.

TLC: Rf 0.36 (toluene:acetone=4:1); $^1$H-NMR(CDCl$_3$):δ 7.60–7.55(2 H,m), 7.45(1 H,d,J=7.7 Hz), 7.35(1 H,t,J=7.7 Hz), 5.91(1 H,bs), 5.00(1 H,s), 4.62(2 H,bs), 4.15–4.05(4 H,m), 3.43–3.25(4 H,m), 2.36(6 H,s), 1.44(18 H,s) FAB-MS (m/z):585 (M+H)$^+$m-nitrobenzyl alcohol matrix; IR(KBr) :3368, 2978, 2230, 1692, 1491, 1213, 1171, 1119 cm$^{-1}$ Reference Example 12

Preparation of 1,4-dihydro-2,6-dimethyl-4-(3-cyanophenyl) pyridine-3,5-dicarboxylic acid bis(2-aminoethyl)ester dihydrochloride 5-dicarboxylic acid bis(2-t-butoxycarbonylaminoethyl) ester prepared in Reference Example 11 to obtain 201 mg (yield 61%) of the target compound.

TLC: Rf 0.43 (butanol:acetic acid:water=4:1:1); $^1$H-NMR(D$_2$O): δ 7.74–7.68(2 H,m), 7.61(1 H,d,J=7.7 Hz), 7.49(1 H,t,J=7.7 Hz), 4.99(1 H,s), 4.44–4.28(4 H,m), 3.36–3.30(4 H,m), 2.35(6 H,s) FAB-MS(m/z):385(M+H)$^+$ glycerol matrix; Ik(KBr):3434, 3013, 2228, 1711, 1495, 1273, 1209, 1113, 1092 cm$^{-1}$ Reference Example 13

Preparation of 1,4-dihydro-2,6-dimethyl-4-(2-nitrophenyl) pyridine-3,5-dicarboxylic acid bis(2-t-butoxycarbonylaminoethyl) ester

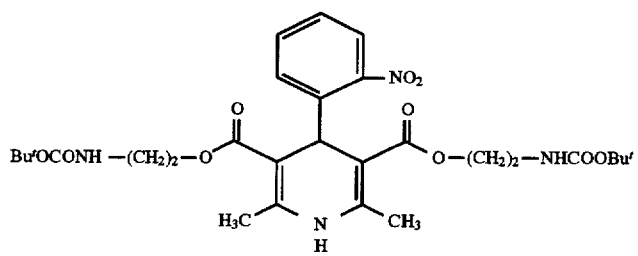

The reaction, treatment and purification procedures of Reference Example 5 were repeated except for using 339 mg of 3-nitrobenzaldehyde to obtain 779 mg (yield 63%) of the target compound.

TLC: Rf 0.26 (toluene:acetone=4:1); $^1$H-NMR(CDCl$_3$):δ 7.71(1 H.d.J=7.7 Hz), 7.53–7.46(2 H.m), 7.31–7.26(1 H.m), 5.94(1 H.bs), 5.81(1 H.s), 4.83(2 H.bs), 4.23–3.96(4 H.m), 3.35–3.25(4 H.m), 2.34(6 H.s), 1.43(18 H.s) FAB-MS(m/z): 605(M+H)$^{3O}$ m-nitrobenzyl alcohol matrix; IR(KBr)=3391, 2978, 1698, 1532, 1497, 1213, 1171, 1115 cm$^{-1}$ Reference Example 14

Preparation of 1,4-dihydro-2,6-dimethyl-4-(2-nitrophenyl)pyridine-3,5-dicarboxylic acid bis(2-aminoethyl) ester dihydrochloride

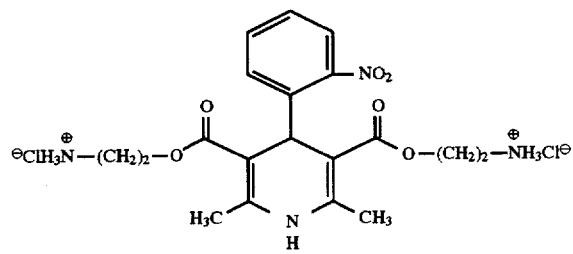

The reaction, treatment and purification procedures of Reference Example 6 were repeated except for using 418 mg of 1,4-dihydro-2,6-dimethyl-4-(2-nitrophenyl)pyridine-3,5-dicarboxylic acid bis(2-t-butoxycarbonylaminoethyl) ester prepared in Reference Example 13 to obtain 271 mg (yield 82%) of the target compound.

Silica gel TLC: Rf 0.40 (butanol:acetic acid:water=4:1:1); $^1$H-NMR(D$_2$O):δ 7.83–7.80(1 H.m), 7.70–7.62(2 H.m), 7.46–7.40(1 H.m), 5.65(1 H.s), 4.43–4.16(4 H.m), 3.32–3.27(4 H.m), 2.32(6 H.s) FAB-MS(m/z):405(M+H)$^+$ glycerol matrix; IR(KBr):3432, 1696, 1524, 1489, 1209, 1111 cm$^{-1}$ Reference Example 15

Preparation of 1,4-dihydro-2,6-dimethyl-4-(3-nitrophenyl)pyridine-3,5-dicarboxylic acid bis(2-phthaloylaminoethyl) ester To a solution of 1.0 g of 2-phthaloylaminoethanol in 2 ml of tetrahydrofuran were added 0.036 ml of triethylamine and then a solution of 0.45 ml of diketene in 0.5 ml of tetrahydrofuran dropwise, followed by stirring the mixture at 55° C. for 1 hour. The reaction mixture was concentrated under reduced pressure. The crude acetoacetic acid ester thus obtained was dissolved in 2 ml of an aqueous 95% ethanol solution and 200 mg of ammonium carbonate was added to the resulting slution, followed by stirring the mixture at 40° C. for 2 hours. To the reaction mixture were added 480 mg of m-nitrobenzaldehyde, 80 mg of citric acid, and 1 ml of water and the mixture was heated to reflux for 4 hours in an oil bath at 90° C. The residue obtained after concentration of the reaction mixture was dissolved in 50 ml of ethyl acetate and the solution was washed with water. The organic phase was dried over anhydrous sodium sulfate. The residue after concentration of the organic phase under reduced pressure was purified through a column filled with 50 ml of silica gel with a toluene/ethyl acetate mixed solution (mixing ratio= 5:1) as a developer to obtain 1.02 g of the target compound.

TLC: Rf 0.25 (toluene:ethyl acetate=2:1); $^1$H-NMR (CDCl$_3$):δ 8.04(1 H.s), 7.80(4 h.m), 7.8–7.7(5 H.m), 7.55(1 H.d.J=7.7 Hz), 7.08(1 H.t.J=7.7 Hz), 5.89(1 H.br), 4.96(1 H.s), 4.33–4.22(4 H.m), 4.06–3.99(2 H.m), 3.90–3.84(2 H.m), 2.31(6 H.s); FAB-MS(m/z):665(M+H)$^+$m-nitrobenzyl alcohol matrix; Melting point: 233° ~236° C.

Example 1

Preparation of 1,4-dihydro-2,6-dimethyl-4-(3-nitrophenyl)pyridine-3,5-dicarboxylic acid bis[2-(2-carboxylbenzoyl)aminoethyl] ester

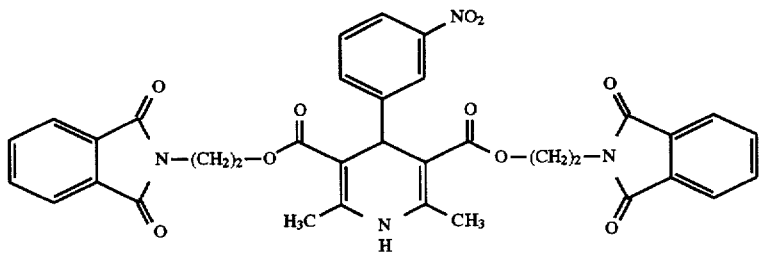

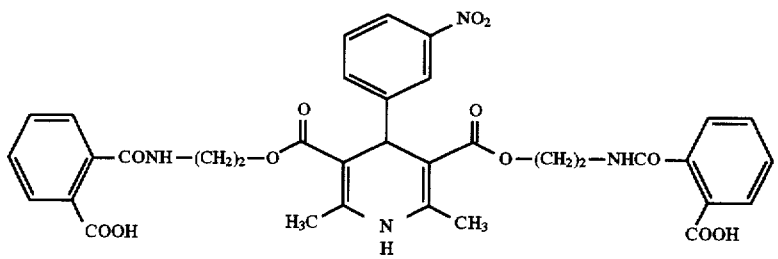

To a solution of 1.0 g of 1,4-dihydro-2,6-dimethyl-4-(3-nitrophenyl)pyridine-3,5-dicarboxylic acid bis(2-phthaloylaminoethyl) ester dissolved in 20 ml of acetone was added 20 ml of an aqueous 20% sodium cafrbonate solution, and the mixture was stirred with heating at 50 to 60° C. for 3 hours. To the reaction mixture was added 20 ml of water and acetone was distilled off under reduced pressure, followed by addition of 20 ml of ethyl acetate and separation. To the aqueous phase was added 50 ml of an aqueous 1N hydrochloric acid solution to adjust the solution to pH 2. Thereafter, the reaction mixture was separated and extracted with 100 ml of ethyl acetate. The organic phase was washed with water and dried over anhydrous sodium sulfate, followed by distilling off the solvent under reduced pressure to obtain 980 g of the target compound.

$^1$H-NMR(CD$_3$IOD):δ 8.13(1 H,t,J=2.2 Hz), 7.92(2 H,d, J=7.7 Hz), 7.87(1 H,d,J=7.7 Hz), 7.71(1 H,d,J=7.7 Hz), 7.57–7.48(4 H,m), 7.33(2 H,d,J=7.7 Hz), 7.28(1 H,t,J=8.1 Hz), 5.15(1 H,s), 4.25–4.19(2 H,m), 4.16–4.11(2 H,m), 3.64–3.57(2 H,m), 3.50–3.43(2 H,m), 2.34(6 H,s); FAB-MS (M/z):699(M-H)$^-$ m-nitrobenzyl alcohol matrix ; Melting point: 136–139° C.

Reference Example 16

Preparation of 1,4-dihydro-2,6-dimethyl-4-(2-chlorophenyl) pyridine-3,5-dicarboxylic acid bis(2-phthaloylaminoethyl) ester The reaction, treatment and purification procedures of Reference Example 15 were repeated except for using 608 mg of 2-chlorobenzaldehyde to obtain 1.62 g of the target compound.

TLC: Rf 0.21 (toluene:ethyl acetate=2:1); $^1$H-NMR (CDCl$_3$):δ 7.81(4 h,dd,J=5.5 Hz,3.3 Hz), 7.71(4 H,dd,J=5.5 Hz,3.3 Hz), 7.30(1 H,d,J=7.7 Hz), 6.99–6.95(1 H,m), 6.72–6.69(2 H,m), 5.61(1 H,s), 5.11(1 H,s), 4.27–4.21(2 H,m), 4.18–4.12(2 H,m), 3.96–3.86(2 H,m), 3.84–3.77(2 H,m), 2.28(6 H,s); FAB-MS (m/z):654 (M+H)$^{+m}$-nitrobenzyl alcohol matrix Example 2

Preparation of 1,4-dihydro-2,6-dimethyl-4-(2-chlorophenyl) pyridine-3,5-dicarboxylic acid bis[2-(2-carboxybenzoyl) aminoethyl] ester

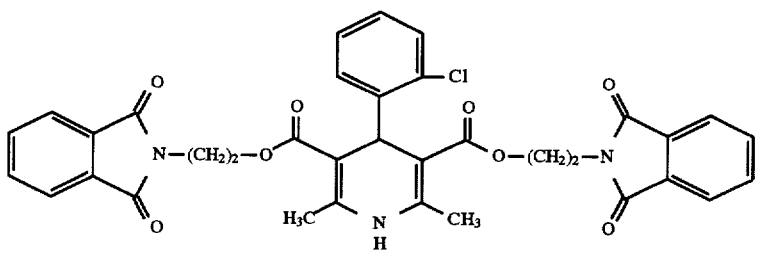

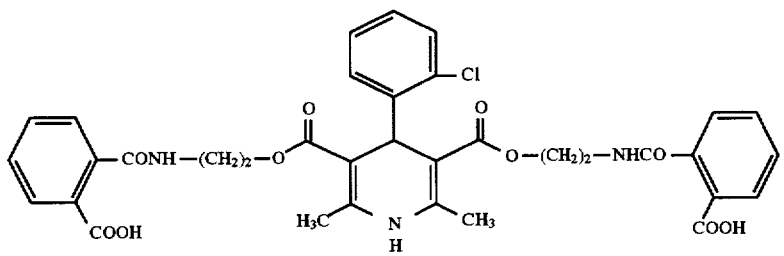

The reaction, treatment and purification procedures of Example 1 were repeated except for using 500 mg of 1,4-dihydro-2,6-dimethyl-4-(2-chlorophenyl) pyridine-3,5-dicarboxylic acid bis(2-phthaloylaminoethyl) ester prepared in Reference Example 16 to obtain 338 mg of the target compound. $^1$H-NMR(CD$_3$OD):δ 7.93(2 H,d,J=7.7 Hz), 7.60–7.50(4 h,m), 7.40(1 H,d,J=8.1 Hz), 7.36(2 H,d,J=7.7 Hz), 7.06(2 H,t,J=8.1 Hz), 6.92(1 H,t,J=8.1 Hz), 5.41(1 H,s), 4.23–4.18(2 H,m), 4.15–4.10(2 H,m), 3.62–3.56(2 H,m), 3.53–3.47(2 H,m), 2.28(6 H,s); FAB-MS (m/z):688 (M-H) ⁻m-nitorobenzyl alcohol matrix Reference Example 17
Preparation of 1,4-dihydro-2,6-dimethyl-4-(3-chlorophenyl) pyridine-3,5-dicarboxylic acid bis(2-phthaloylaminoethyl) ester

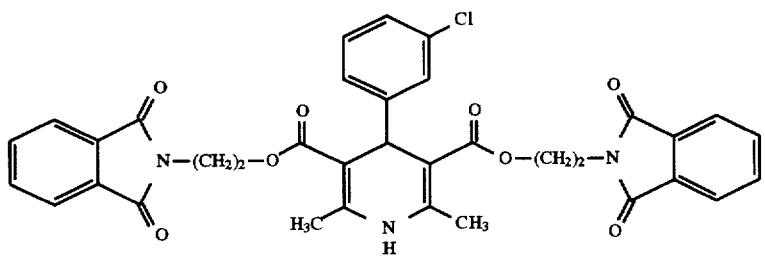

The reaction, treatment and purification procedures of Reference Example 15 were repeated except for using 608 mg of 3-chlorobenzaldehyde to obtain 1.85 g of the target compound.

TLC: Rf 0.21 (toluene:ethyl acetate=2:1); $^1$H-NMR (CDCl$_3$):δ 7.83(4 h,dd,J=5.5 Hz,3.3 Hz), 7.71(4 h,dd,J=5.5 Hz,3.3 Hz), 7.12(1 H,s), 7.06–7.03(1 H,m), 6.82–6.81(2 H,m), 5.63(1 H,s), 4.84(1 H,s), 4.35–4.30(2 H,m), 4.26–4.20(2 H,m), 4.05–3.98(2 H,m), 3.92–3.86(2 H,m), 2.29(6 H,s) FAE-MS(m/z):654(M+H)$^+$m-nitrobenzyl alcohol matrix Example 3

Preparation of 1,4-dihydro-2,6-dimethyl-4-(3-chlorophenyl) pyridine-3,5-dicarboxylic acid bis[2-(2-carboxybenzoyl) aminoethyl] ester

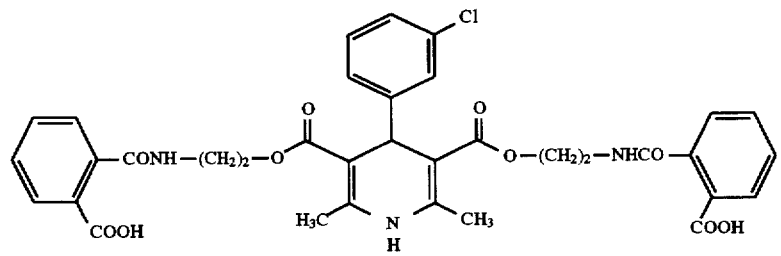

The reaction, treatment and purification procedures of Example 1 were repeated except for using 500 mg of 1,4-dihydro-2, 6-dimethyl-4- (3-chlorophenyl)pyridine-3,5-dicarboxylic acid bis(2-phthaloylaminoethyl) ester prepared in Reference Example 17 to obtain 399 mg of the target compound.

$^1$H-NMR(CD$_3$OD): δ 7.94–7.91(2 H,m), 7.58–7.49(4 H,M), 7.35–7.33(2 H,m), 7.23–7.19(2 H,m), 7.03–6.95(2

H,m), 5.02(1 H,s), 4.25–4.14(4 H,m), 3.63–3.58(2 H), 3.52–3.47(2 H), 2.29(6 H,s) FAB-MS(m/z):688 (M-H)⁻ m-nitrobenzyl alcohol matrix

Reference Example 18

Preparation of 1,4-dihydro-2,6-dimethyl-4-(2,3-dichlorophenyl)pyridine-3,5-dicarboxylic acid bis(2-phthaloylaminoethyl) ester

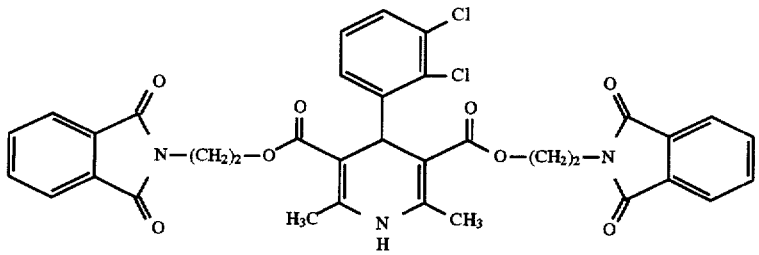

The reaction, treatment and purification procedures of Reference Example 15 were repeated except for using 763 mg of 2,3-dichlorobenzaldehyde to obtain 1.04 g of the target compound.

TLC: Rf 0.21 (toluene:ethyl acetate=2:1); ¹H-NMR (CDCl₃): δ 7.80(4 H,,dd,J=5.5 Hz,3.3 Hz), 7.71(4 H,dd,J= 5.5 Hz,3.3 Hz), 7.26–7.25(1 H,m), 7.23(1 H,d,J=2.2 Hz), 6.89(1 H,t,J=7.7 Hz), 6.83(1 H,d,J=7.7 Hz), 5.61(1 H,s), 5.17(1 H,s), 4.11–4.26(4 H,m), 3.98–3.91(2 H), 3.83–3.77(2 H), 2.28(6 H,s); FAB-MS(m/z):688 (M+H)⁺ m-nitrobenzyl alcohol matrix

Example 4

Preparation of 1,4-dihydro-2,6-dimethyl-4-(2,3-dichlorophenyl)pyridine-3,5-dicarboxylic acid bis[2-(2-carboxybenzoyl)aminoethyl] ester

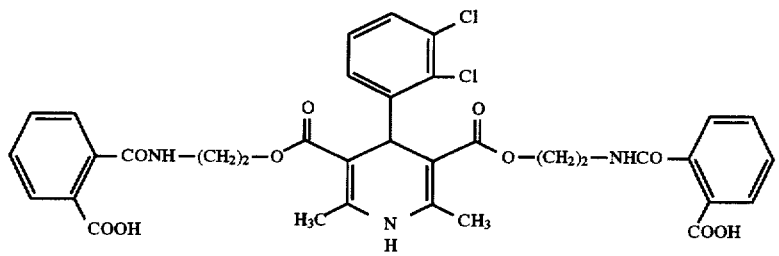

The reaction, treatment and purification procedures of Example 1 were repeated except for using 500 mg of the 1,4-dihydro-2,6-dimethyl-4-(2,3-dichlorophenyl)pyridine-3,5-dicarboxylic acid bis(2-phthaloylaminoethyl)ester prepared in Reference Example 18 to obtain 302 mg of the target compound. ¹H-NMR(CD₃OD): δ 7.93(2 H,dd,J=7.7 Hz,1.5 Hz), 7.57(2 H,td,J=7.7 Hz,1.5 Hz), 7.51(2 H,td,J=7.7 Hz, 1.5 Hz), 7.38(3 H,m), 7.18(1 H,dd,J=8.1 Hz,1.8 Hz), 7.06(1 H,t,J=8.1 Hz), 5.49(1 H,s), 4.26–4.20(2 H), 4.13–4.08(2 H), 3.64–3.57(2 H), 3.52–3.46(2 H), 2.28(6 H,s) FAB-MS (m/z):722 (M-H)⁺ m-nitrobenzyl alcohol matrix

Reference Example 19

Preparation of 1,4-dihydro-2,6-dimethyl-4-(3-cyanophenyl)pyridine-3,5-dicarboxylic acid bis(2-phthaloylaminoethyl) ester

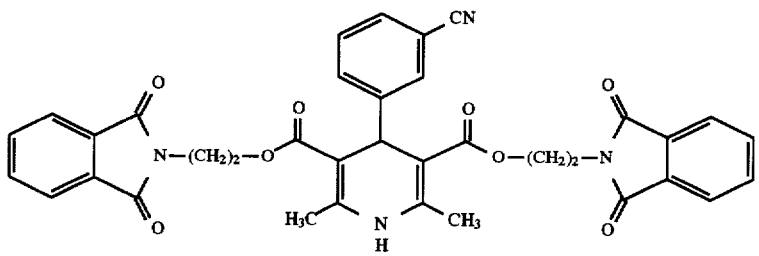

The reaction, treatment and purification procedures of Reference Example 15 were repeated except for using 572 mg of 3-cyanophenylbenzaldehyde to obtain 2.00 g of the target. compound.

$^1$H-NMR(CDCl$_3$): δ 7.84(4 H,dd,J=5.5 Hz,3.3 Hz), 7.73(4 H,dd,J=5.5 Hz,3.3 Hz), 7.47–7.44(2 H, m), 7.15(1 H,d,J=7.7 Hz), 7.00(1 H,t,J=7.7 Hz), 5.70(1 H,s), 4.87(1 H,s), 4.34–4.21(4 H,m), 4.03–3.97(2 H,m), 3.91–3.85(2 H), 2.30(6 H,s); FAB-MS(m/z):645(M+H)$^+$m-nitrobenzyl alcohol matrix The reaction, treatment and purification procedures of Reference Example 15 were repeated except for using 660 mg of 2-nitrobenzaldehyde to obtain 958 mg of the target compound.

$^1$H-NMR(CDCl$_3$): δ 7.78(4 H,dd,J=5.5 Hz,3.3 Hz), 7.70(4 H,dd,J=5.5 Hz,3.3 Hz), 7.44(1 H,d,J=8.1 Hz), 7.33(1 H,t,J=7.7 Hz), 7.16(1 H,d,J=8.1 Hz), 6.92(1 H,t,J=7.7 Hz), 5.71(1 H,s), 5.43(1 H,s), 4.24–4.10(4 H,m), 3.90–3.74(4 H,m), 2.30(6 H,s); FAB-MS(m/z):665(M+H)$^+$m-nitrobenzyl alcohol matrix Example 5
Preparation of 1,4-dihydro-2,6-dimethyl-4-(3-cyanophenyl)pyridine-3,5-dicarboxylic acid bis[2-(2-carboxybenzoyl)aminoethyl] ester Example 6
Preparation of 1,4-dihydro-2,6-dimethyl-4-(2-nitrophenyl)pyridine-3,5-dicarboxylic acid bis[2-(2-carboxybenzoyl)aminoethyl] ester

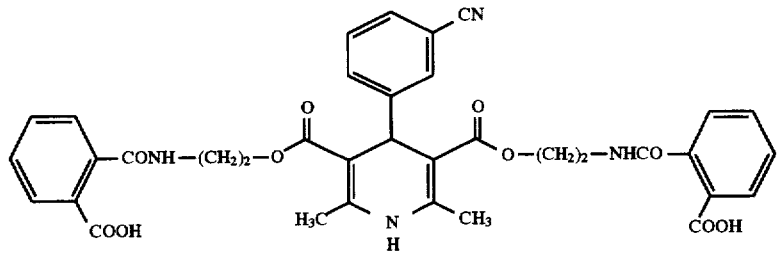

The reaction, treatment and purification procedures of Example 1 were repeated except for using 500 mg of the 1,4-dihydro-2,6-dimethyl-4-(3-cyanophenyl)pyridine-3,5-dicarboxylic acid bis(2-phthaloylaminoethyl) ester prepared in Reference Example 19 to obtain 429 mg of the target compound.

$^1$H-NMR(CD$_3$OD): δ 7.93(2 H,d,J=7.7 Hz), 7.61(1 H,t, J=8.0 Hz), 7.57–7.49(5 H,m), 7.37–7.33(3 H,m), 7.23(1 H,t,J=7.7 Hz), 5.07(1 H,s), 4.26–4.20(2 H,m), 4.16–4.09(2 H,m), 3.63–3.56(2 H, m), 3.50–3.44(2 H), 2.33(6 H,s); FAB-MS(m/z):679(M–H)$^-$m-nitrobenzyl alcohol matrix Reference Example 20
Preparation of 1,4-dihydro-2,6-dimethyl-4-(2-nitrophenyl)pyridine-3,5-dicarboxylic acid bis(2-phthaloylaminoethyl) ester

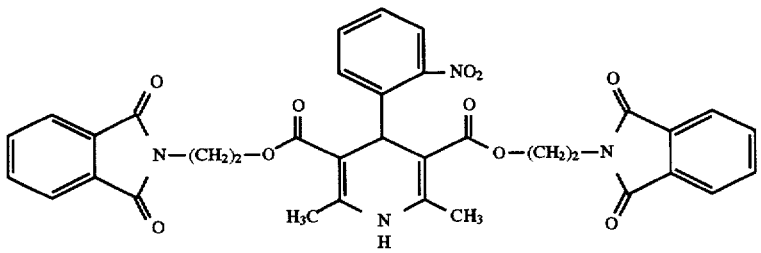

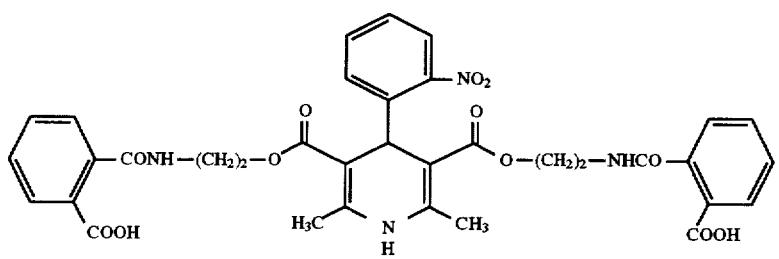

The reaction, treatment and purification procedures of Example 1 were repeated except for using 500 mg of the 1,4-dihydro-2,6-dimethyl-4-(2-nitrophenyl)pyridine-3,5-dicarboxylic acid bis(2-phthaloylaminoethyl) ester prepared in Reference Example 20 to obtain 239 mg of the target compound.

$^1$H-NMR(CD$_3$OD): δ 7.92(2 H,d,J=7.3 Hz), 7.59–7.44(7 H, m), 7.38(2 H,d,J=7.3 Hz), 7.19(1 H,t,J=7.3 Hz), 5.75(1 H,s), 4.30–4.24(2 H), 4.08–4.02(2 H), 3.54–3.51(4 H,m), 2.30(6 H,s) FAB-MS(m/z):699(M–H)⁻ m-nitrobenzyl alcohol matrix

Reference Example 21

Preparation of 1,4-dihydro-2,6-dimethyl-4-(3-nitrophenyl) pyridine-3,5-dicarboxylic acid bis(3-phthaloylaminopropyl) ester

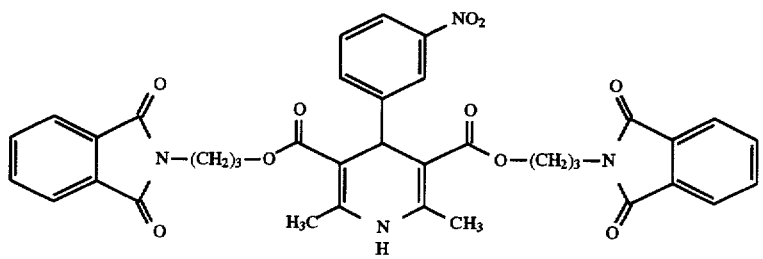

To a solution of 3.0 g of 3-phthaloylaminopropanol in 6 ml of tetrahydrofuran were added 0.1 ml of triethylamine and then a solution of 1.5 ml of diketene in 2 ml of tetrahydrofuran dropwise, followed by stirring the mixture at 55° C. for 1 hour. The reaction mixture was concentrated under reduced pressure to form crude acetoacetic acid ester, which then was dissolved in 6 ml of an aqueous 90% ethanol solution and 562 mg of ammonium carbonate was added to the resulting solution, followed by stirring the mixture at 40° C. for 2 hours. To the reaction mixture were added 1.33 g of m-nitrobenzaldehyde, 230 mg of citric acid, and 1.5 ml of water and the mixture was heated to reflux for 4 hours in an oil bath at 90° C. The residue obtained after concentration of the reaction mixture was dissolved in 200 ml of ethyl acetate and the solution was washed with water. The organic phase was dried over anhydrous sodium sulfate. The residue after concentration of the organic phase under reduced pressure was purified through a column filled with 200 ml of silica gel with a toluene/ethyl acetate mixed solution (mixing ratio= 5:1) as a developer to obtain 2.51 g of the target compound.

TLC: Rf 0.24 (toluene:ethyl acetate=2:1) $^1$H-NMR (CDCl$_3$): δ 8.18(1 H,t,J=1.8 Hz), 7.99(1 H,d,J=7.7 Hz), 7.83(1 H,d,J=7.7 Hz), 7.78(4 H,dd,J=5.5 Hz,3.3 Hz), 7.67(4 H,dd,J=5.5 Hz,3.3 Hz), 7.43(1 H,t,J=7.7 Hz), 6.09(1 H,s), 5.17(1 H,s), 4.15–4.08(4 H,m), 3.77–3.74(4 H,m), 2.39(6 H,s), 2.08–2.01(4 H,m); FAB-MS(m/z):693(M+H)⁺ m-nitrobenzyl alcohol matrix

Example 7

Preparation of 1,4-dihydro-2,6-dimethyl-4-(3-nitrophenyl) pyridine-3,5-dicarboxylic acid bis[3-(2-carboxybenzoyl) aminopropyl] ester

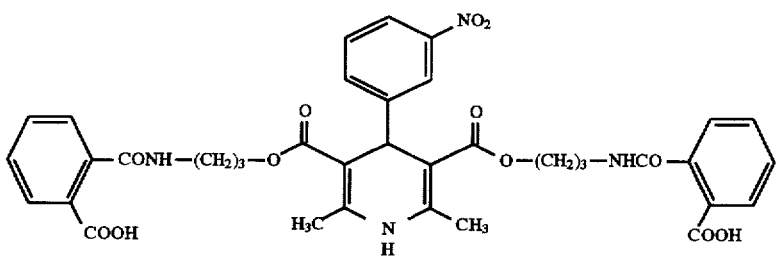

The reaction, treatment and purification procedures of Example 1 were repeated except for using 1 g of the 1,4-dihydro-2, 6-dimethyl-4- (3-nitrophenyl)pyridine-3,5-dicarboxylic acid bis(3-phthaloylaminopropyl) ester prepared in Reference Example 21 to obtain 504 mg of the target compound.

¹H-NMR(CD₃OD): δ 8.13(1 H,t,J=1.8 Hz), 8.00(1 H,d, J=8.1 Hz), 7.92(2 H,dd,J=7.3 Hz, 1.5 Hz), 7.74(1 H,d,J=7.7 Hz), 7.57-7.46(5 H,m), 7.38(2 H,dd,J=7.3 Hz,1.5 Hz), 5.12(1 H,s), 4.15(4 H,t,J=6.2 Hz), 3.36(4 H,t,J=6.6 Hz), 2.35(6 H,s), 1.99-1.89(4 H,m); FAB-MS(m/z):727(M-H)⁻ m-nitrobenzyl alcohol matrix Reference Example 22

Preparation of (4R)-1,4-dihydro-2,6-dimethyl-3-(2-aminoethyl)oxycarbonyl-4-(3-nitrophenyl) pyridine-5-carboxylic acid (microbiological method)

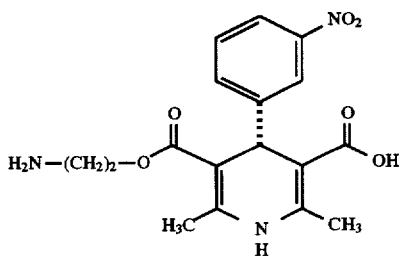

30 mg of the 1,4-dihydro-2,6-dimethyl-4-(3-nitrophenyl) pyridine-3,5-dicarboxylic acid bis(2-aminoethyl) ester dihydrochloride prepared in Reference Example 4 was dissolved in 0.5 ml of 0.5M phosphate buffer solution (pH 8.0). In this solution was added 0.5 ml of the supernatant of centrifuged culture liquor prepared as described hereinbelow in which Streptomyces viridosporus A-914 strain was cultivated, and the mixture was allowed to react for 48 hours on a shaker. Then, the reaction mixture was passed through a column packed with 5 ml of DIAION HP-20 (Mitsubishi Chemical Industries, Co., Ltd.) for adsorption. After it was washed with 10 ml of deionized water and 10 mol of aqueous 20% methanol solution, the column was eluted with 20 ml of aqueous 40% methanol solution and the fractions containing the target compound which developed a color with ninhydrin at Rf 0.61 on TLC (n-butanol:acetic acid:water=4:1:1) were collected and concentrated to dryness to obtain 12.4 mg of the target compound.

¹H-NMR(CD₃OD): δ 8.12(1 H,t,J=2.0 Hz) 7.97(1 H,dd, J=8.0 Hz,2.4 Hz), 7.67(1 H,d,J=8.0 Hz), 7.43(1 H,t,J=8.0 Hz), 5.26(1 H,s), 4.26(1 H,m), 3.97(1 H,m), 3.06(2 H,t,J=5.4 Hz), 2.36(3 H,s), 2.23(3 H,s); FAB-MS(m/z):362(M+H)⁺m-nitrobenzyl alcohol matrix

[Cultivation of Streptomyces viridosporus A-914 strain]

Streptomyces viridosporus A-914 strain was inoculated in a 250 ml flask containing 30 ml of C medium (2% of potato starch, 2% of Soybean meal, 0.5% of yeast extract, 0.25% of sodium chloride, 0.32% of calcim carbonate, 0.0005% of ferrous sulfate heptahydride, 0.0005% of manganese sulfate tetrahydride, 0.0005% of zinc sulfate heptahydride, pH 7.4) and incubated at 28° C. for 3 days, followed by centrifugation at 5,000 rpm for 10 minutes to obtain a fungal culture.

Reference Example 23

Measurement of optical purity of (4R)-1,4-dihydro-2,6-dimethyl-3-(2-aminoethyl) oxycarbonyl-4-(3-nitrophenyl) pyridine-5-carboxylic acid

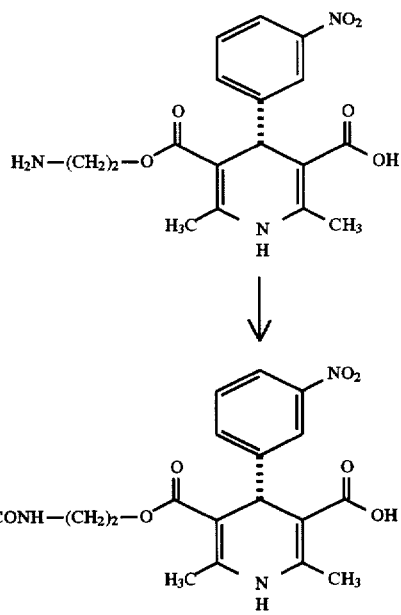

The compound of Reference Example 22 was converted to the known compound, (4R)-3-(2-acetamidoethyl) oxycarbonyl1,4-dihydro-2,6-dimethyl-4-(3-nitrophenyl) pyridine-5-carboxylic acid (W094/05637) in the following manner, before its optical purity could be measured.

That is, 10 mg of the (4R)-1,4-dihydro-2,6-dimethyl3-(2-aminoethyl) oxycarbonyl-4-(3-nitrophenyl)pyridine-5-carboxylic acid obtained in Example 28 was dissolved in 2 ml of deionized water and 0.2 ml of acetic anhydride was added to the solution while stirring at room temperature. After stirring for continuous 30 minutes, the reaction mixture was extracted 3 times with 5 ml each of ethyl acetate and washed with 10 ml of saturated saline. The ethyl acetate layer was adsorbed on a preparatory TLC plate, developed with chloroform/methanol (7:1) to elute fractions showing UV absorption at Rf 0.22. The eluate was evaporated to dryness to obtain 3.7 mg of (4R)-3-(2-acetamidoethyl) oxycarbonyl-1,4-dihydro-2,6-dimethyl-4-(3-nitrophenyl) pyridine-5-carboxylic acid. The optical purity of this substance was determined by HPLC(mobile phase: 0.35% isopropanol/0.1M phosphaste buffer solution (pH 4.4), flow rate: 0.8 ml/minute) using an otical resolution column: CHIRAL AGP (4 mm×100 mm) manufactured by Daicel Chemical Industries Ltd. As a result, it revealed that the optical purity of the 4R form was 100% and the retention time was 14.3 minutes.

¹H-NMR(CDCl₃): δ 8.11(1 H,t,J=2.0 Hz), 7.99(1 H,dd, J=8.0 Hz,2.4 Hz), 7.66(1 H,d,J=8.0 Hz), 7.44(1 H,t,J=8.0 Hz), 5.10(1 H,s), 4.2-4.0(2 H), 3.40(2 H,t,J=5.5 Hz), 2.34(6 H,s), 1.91(3 H,s)

Example 8

Preparation of (4R)-1,4-dihydro-2,6-dimethyl-3-[2-(2-carboxybenzoyl) aminoethyl]oxycarbonyl-4-(3-nitrophenyl)pyridine-5-carboxylic acid (enzymatic method)

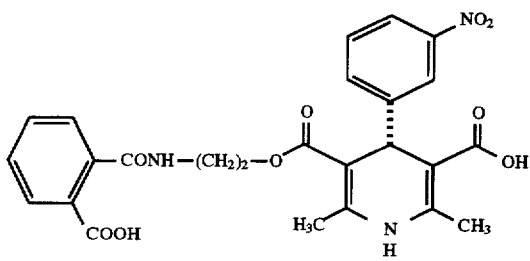

To an aquous solution of 50 mg of 1,4-dihydro-2,6-dimethyl-4-(3-nitrophenyl) pyridine-3,5-dicarboxylic acid bis[2-(2-carboxybenzoyl)aminoethyl] ester, pH 9, was added 50 mg of protease P-6 (Amano Pharmaceutical Co., Ltd.) and the mixture was stirred at 28° C. for 23 hours. After the reaction mixture was made acidic with 1N aqueous hydrochloric acid solution, 20 ml of ethyl acetate was added thereto. The ethyl acetate layer was washed with water, dried over sodium sulfate and concentrated under reduced pressure. The residue was subjected to preparatory TLC to obtain 17.1 mg of the target compound.

$^1$H-NMR(CD$_3$OD): δ 8.14(1 H,t,J=2.2 Hz), 7.92(1H,d,J= 8.1 Hz), 7.69–7.66(2 H), 7.44–7.33(4 H,m), 5.13(1 H,s), 4.23–4.16(2 H), 3.58–3.50(2 H), 2.35(3 H,s), 2.31(3 H,s); FAB-MS(m/z):508(M–H)$^-$

Example 9

Preparation of (4R)-1,4-dihydro-2,6-dimethyl-3-[2-(2-carboxybenzoyl) aminoethyl]oxycarbonyl-4-(3-nitrophenyl) pyridine-5-carboxylic acid (microbiological method)

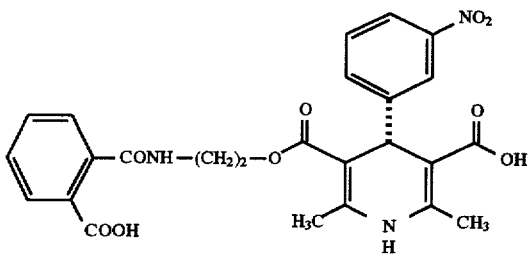

One loopful of a slant culture of FERM P-13098 (A-914 strain) was inoculated in a 250 ml Erlenmeyer flask containing 30 ml of a seed culture (2% of potato starch, 2% of glucose, 2% of Soybean meal, 0.5% of yeast extract, 0.25% of sodium chloride, 0.32% of calcim carbonate, 0.0005% of ferrous sulfate heptahydride, 0.0005% of manganese sulfate tetrahydride, 0.0005% of zinc sulfate heptahydride, pH 7.4) and incubated at 28° C. for 2 days on a rotary shaker to prepare a seed culture.

1 ml of the seed culture thus cultivated was charged in a 500 ml Erlenmeyer flask containing 100 ml of a production medium having the same composition as the seed culture medium and incubated at 28° C. for 5 days. The culture liquor thus obtained was filtered to give 80 ml of the filtrate.

In 50 ml of the filtrate of the culture liquor was dissolved 1.0 g of 1,4-dihydro-2,6-dimethyl-4-(3-nitrophenyl) pyridine-5-carboxylic acid bis[2-(2-carboxybenzoyl) aminoethyl] ester and the solution was stirred at 40° C. for 72 hours in a reaction vessel equipped with a pH stat while adjusting the solution to pH 8.5 to 8.6 with an aqueous 1N sodium hydroxide solution. The reaction mixture was adjusted to pH 3.0 with 1N hydrochloric acid and then extracted twice with 100 ml each of ethyl acetate. The ethyl acetate layer was washed with 50 ml of saturated saline and then dried over anhydrous sodium sulfate. After filtration of the desiccant, the ethyl acetate layer was concentrated to dryness to give yellow solids. The mixture was adsorbed on a preparatory TLC plate, developed with ethyl acetate/ methanol/acetic acid (10:2:0.1) to elute fractions showing UV absorption at Rf 0.36. The eluate was evaporated to dryness under reduced pressure to obtain 350 mg of (4R)-1,4-dihydro-2,6-dimethyl-3-[2-(2-carboxybenzoyl) aminoethyl]oxycarbonyl-4-(3-nitrophenyl)pyridine-5-carboxylic acid. The NMR spectrum of the product was the same as that of the compound of Example 8.

Reference Example 24:

Measurement of optical purity of (4R)-1,4-dihydro-2,6-dimethyl-3-[2-(2-carboxybenzoyl) aminoethyl] oxycarbonyl-4-(3-nitrophenyl)pyridine-5-carboxylic acid

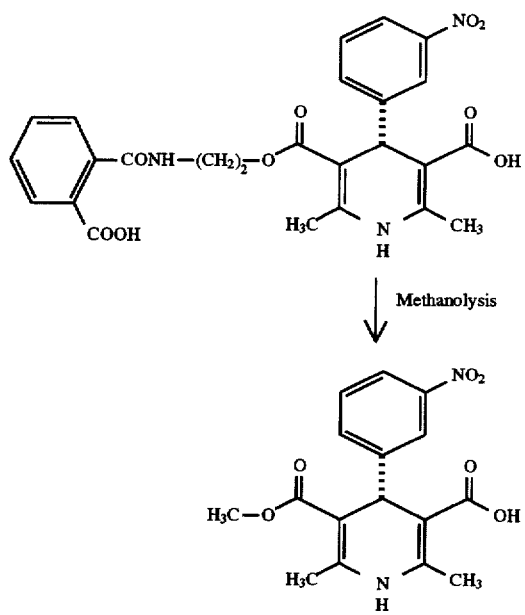

To 50 mg of the (4R)-1,4-dihydro-2,6-dimethyl-3-[2(2-carboxybenzoyl) aminoethyl]oxycarbonyl-4-(3-nitrophenyl)pyridine-5-carboxylic acid obtained in Example 8 was added 5 ml of sodium methoxide (28% methanol solution) and the mixture was stirred at 50° C. for 2 hours. After it was diluted with 10 ml of water, the reaction mixture was washed with 5 ml of ethyl acetate and the aqueous layer was adjusted to pH 3 before it was extracted 3 times with 10 ml each of ethyl acetate. The ethyl acetate layer was dried over anhydrous sodium sulfate and evaporated to dryness. The yellow substance thus obtained was purified on a column packed with 120 ml of Sephadex LH-20 (solvent: methanol) to obtain 22 mg of (4R)-1,4-dihydro-2,6-dimethyl-3-methyloxycarbonyl-4-(3-nitrophenyl) pyridine-5-carboxylic acid. The optical purity of this substance was analyzed by HPLC (mobile phase: hexane:ethanol:acetic acid=90:10:0.1, flow rate: 1.0 ml/minute, detection UV 254 nm) using an otical resolution column: CHIRALPAK AS (4.6 mm ×250 mm) manufactured by Daicel Chemical Industries Ltd. As a result, it revealed that the optical purity of the substance was 100% and the retention time was 12.5 minutes. $^1$H-NMR(CD$_3$OD): δ 8.09(1 H,s), 7.99(1 H,d,J= 9.5 Hz), 7.65(1 H,d,J=7.7 Hz), 7.44(1 H,t,j=8.1 Hz), 5.09(1 H,s), 3.62(3 H,S), 2.34(3 H, s), 2.33(3 H,s)

Example 10

Preparation of (4R)-1,4-dihydro-2,6-dimethyl3-[2-(2-carboxybenzoyl) aminoethyl]oxycarbonyl-4-(3- nitrophenyl)pyridine-5-carboxylic acid (microbiological method)

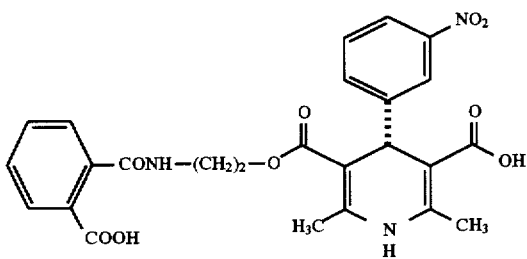

Botryodioplodia sp. FI-741 strain was inoculated in a 250 ml Erlenmeyer flask containing 30 ml of FI medium (2% of potato starch, 2% of Soybean meal, 0.1% of $KH_2PO_4$, 0.05% of magnesium sulfate heptahydride, 1% of glucose, 0.05% of adekanol LG109) and incubated at 28° C. for 3 days.

To the culture liquor was added a solution of 100 mg of 1,4-dihydro-2,6-dimethyl-4-(3-nitrophenyl) pyridine-3,5-dicarboxylic acid bis[2-(2-carboxybenzoyl)aminoethyl] ester in 0.75 ml of deionized water, and shaked for continuous 2 days at 28° C. to obtain 30 mg of (4R)-1,4-dihydro-2,6-dimethyl-3-[2-(2-carboxybenzoyl) aminoethyl] oxycarbonyl-4-(3-nitrophenyl)pyridine-5-carboxylic acid by the same procedures as of Example 9.

Example 11

Preparation of (4R)-1,4-dihydro-2,6-dimethyl3-[2-(2-carboxybenzoyl) aminoethyl]oxycarbonyl-4-(2,3-dichlorophenyl)pyridine-5-carboxylic acid

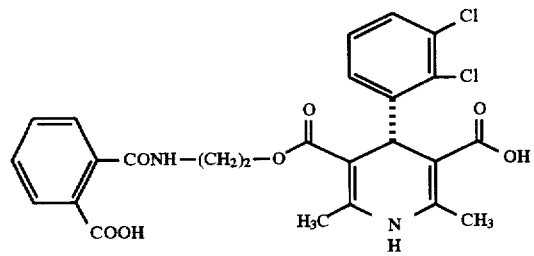

The reaction, treatment and purification procedures of Example 8 were repeated except for using 50 mg of the 1,4-dihydro-2,6-dimethyl-4-(2,3-dichlorophenyl)pyridine3,5-dicarboxylic acid bis[2-(2-carboxybenzoyl)aminoethyl] ester to obtain 3.4 mg of the target compound. $^1$H-NMR ($CDCl_3$): δ 7.74–7.71(1 H,m), 7.44–7.43(3 H,m), 7.35(1 H,dd,J=8.1 Hz, 1.5 Hz), 7.22(1 H,dd,J=7.7 Hz,1.5 Hz), 7.08(1 H,t,J=7.7 Hz), 5.48(1 H,s), 4.26–4.20(1 H,m), 4.13–4.07(1 H,m), 3.61–3.52(2 H), 2.28(3 H,s), 2.24(3 H,s) FAB-MS(m/z):531(M–H)$^-$ Example 12

Preparation of (4R)-1,4-dihydro-2,6-dimethyl3-[2-(2-carboxybenzoyl) aminoethyl]oxycarbonyl-4-(3-chlorophenyl)pyridine-5-carboxylic acid

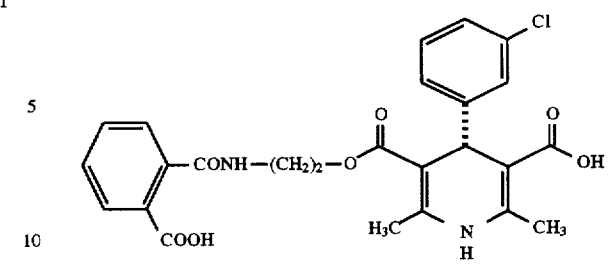

The reaction, treatment and purification procedures of Example 8 were repeated except for using 50 mg of 1,4-dihydro-2,6-dimethyl-4-(3-dichlorophenyl) pyridine-3,5-dicarboxylic acid bis[2-(2-carboxybenzoyl)aminoethyl]ester prepared in Example 3 to obtain 4.0 mg of the target compound.

$^1$H-NMR($CD_3OD$): δ 7.68–7.66(1 H,m), 7.43–7.37(3 H,m), 7.21–7.17(2 H), 7.09–7.01(2 H), 5.02(1 H,s), 4.26–4.16(2 H), 3.59–3.57(2 H), 2.33(3 H,s), 2.28(3 H,s) FAB-MS(m/z):497 (M–H)$^-$

Example 13

Preparation of (4R)-1,4-dihydro-2,6-dimethyl3-[2-(2-carboxybenzoyl) aminoethyl]oxycarbonyl-4-(3-cyanophenyl) pyridine-5-carboxylic acid

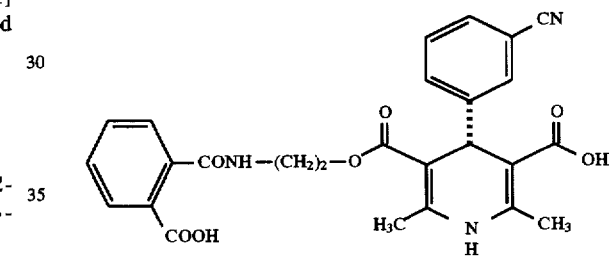

The reaction, treatment and purification procedures of Example 8 were repeated except for using 50 mg of the 1,4-dihydro-2,6-dimethyl-4- (3-cyanophenyl)pyridine-3,5-dicarboxylic acid bis[2-(2-carboxybenzoyl)aminoethyl] ester prepared in Example 5 to obtain 8.2 mg of the target compound.

$^1$H-NMR($CD_3OD$): δ 7.73–7.71(1 H,m), 7.59–7.55(2 H,m), 7.47–7.39(4 H,m), 7.30(1 H,t,J=7.7 Hz), 5.05(1 H,s), 4.28–4.22(1 H,m), 4.20–4.15(1 H,m), 3.59–3.57(2 H,m), 2.34(3 H,s), 2.30(3 H,s) FAB-MS(m/z):488(M–H)$^-$

Example 14

Preparation of (4R)-1,4-dihydro-2,6-dimethyl3-[3-(2-carboxybenzoyl) aminopropyl]oxycarbonyl-4-(3-nitrophenyl)pyridine-5-carboxylic acid

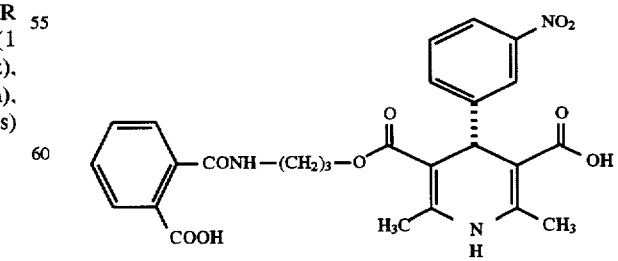

The reaction, treatment and purification procedures of Example 8 were repeated except for using 50 mg of the 1,4-dihydro-2,6-dimethyl-4-(3-nitrophenyl)pyridine-3,5-dicarboxylic acid bis[3-(2-carboxybenzoyl)aminopropyl] ester prepared in Example 7 to obtain 2.8 mg of the target compound.

$^1$H-NMR(CD$_3$OD): δ 8.11(1 H,t,J=1.8 Hz), 8.00–7.97(1 H,m), 7.79–7.77(1 H,m), 7.69(1H,d,J=7.7 Hz), 7.48–7.43(4 H,m), 5.11(1 H,s), 4.15(2 H,t,J=6.2 Hz), 3.35(2 H,t,J=6.2 Hz), 2.36(3 H,s), 2.33(3 H,s), 1.95–1.90(2 H) FAB-MS(m/z):522(M−H)Test$^−$ Test Example 1: Test of Solubility in Water Measurements were made of solubility of the compounds obtained in Reference Example 4, Examples 1 and 7 in 0.05M phosphate buffer solution (PB) (pH 8) and 0.01M phosphate buffer solution (PB) (pH 9). The measurements were performed by mixing 1 to 10 ml of each phosphate buffer solution with 1 to 50 mg of each substrate, stirring the mixture using a magnetic vibrating stirrer for 1 minute and determing critical values (solubility) based on the presence or absence of insoluble matter.

For comparison, measurements in the same manner were made of the solubility of:

A: 1,4-dihydro-2,6-dimethyl-4-(3-nitrophenyl) pyridine-3, 5-dicarboxylic acid bis(2-cyanoethyl) ester

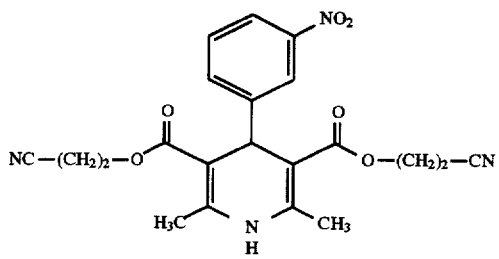

B: 1,4-dihydro-2,6-dimethyl-4-(3-nitrophenyl) pyridine-3, 5-dicarboxylic acid bis(2-methylsulfonylethyl) ester

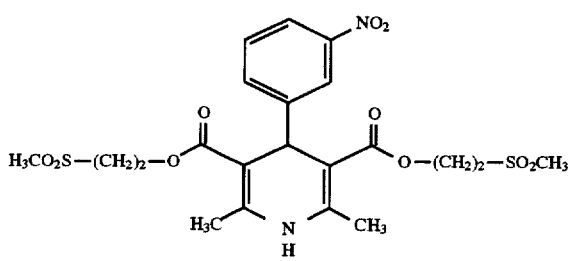

and

C: 1,4-dihydro-2,6-dimethyl-4- (3-nitrophenyl) pyridine-3, 5-dicarboxylic acid bis(2-carbamoylmethyl) ester

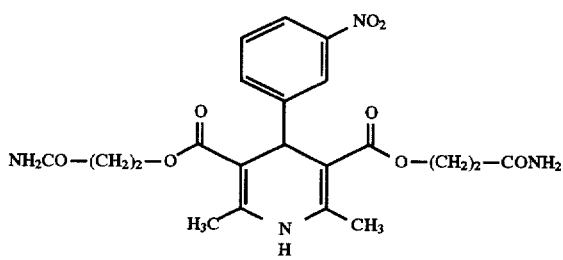

Table 1 shows the results obtained.

TABLE 1

| Solubility of dihydropyridine derivatives (mg/ml) | | |
|---|---|---|
| Substrate Number | 0.05M PB (pH 8) | 0.01M PB (pH 9) |
| Reference Example 4 | 102 | >50 |
| Example 1 | 373 | >50 |
| Example 7 | >50 | >50 |
| A (Comparative) | 0.006 | <0.1 |
| B (Comparative) | 0.109 | <0.1 |
| C (Comparative) | 0.106 | — |

Table 1 shows that the compounds of the present invention have solubility in phosphate buffer solutions which serve as a medium for biochemical reaction much higher than the comparative comounds A, B or C so that reactions can proceed efficiently with the compounds of the present invention.

Test Example 2: Conversion in Enzymatic Reactions

Conversion of the compounds obtained in Reference Example 4 and Example 1 as well as Compound A (comparative compound) described in Test Example 1 above in an asymmetric hydrolysis reaction by crude enzyme from A-914 strain described above.

The reaction was allowed to proceed in a 0.25M phosphate buffer solution (pH 9.0) in a substrate concentration of 10 mg/ml for 48 hours on a shaker kept at 40° C. The reaction mixture was analyzed by HPLC under the conditions below.

HPLC Conditions

[Compound of Reference Example 4 and Comparative Compound A]

Column: YMCA-302 (4.6ID×150mm)

Mobile phase:

0.02M KH$_2$PO$_4$-phosphoric acid (pH 3.0): methanol =60:40, 0.5 ml/min

Detection: UV350 nm

Standard elution time;

Compound of Reference Example 4: 4.3 min, Product: 7.2 min

Comparative Compound A: 10.9 min, Product: 12.3 min

[Compound of Example 1]

Column: Kaseisorb LC ODS SUPER (4.6ID×150 mm)

Mobile phase:

60% Methanol:acetic acid =1000:1, 0.8 ml/min

Detection: UV 254 nm

Standard elution time: 7.9 min, Product: 5.3 min

Table 2 shows the results obtained.

TABLE 2

| Substrate Number | Conversion of Reaction |
|---|---|
| Reference Example 4 | 61.7% |
| Example 1 | 65.3% |
| A (Comparative) | 18.5% |

Table 2 shows that the compounds of the present invention have conversion in asymmetric hydrolysis reactions much higher than the comparative comound A.

We claim:
1. 1,4-dihydropyridine derivatives represented by the formula (I)

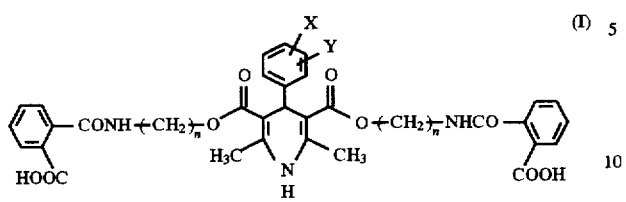

wherein X and Y independently represent a hydrogen atom, a nitro group, a nitrile group or a halogen atom, and n is an integer of 1 to 3 or salts thereof.

2. Optical active 1,4-dihydropyridine derivatives represented by the formula (II)

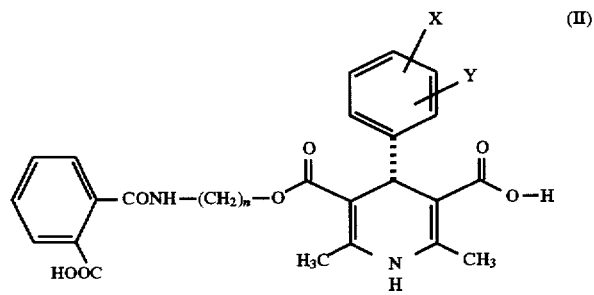

wherein X and Y independently represent a hydrogen atom, a nitro group, a nitrile group or a hydrogen atom; and, n is an integer of 1 to 3 or salts thereof.

3. A method for preparing an optical active 1,4-dihydropyridine derivative represented by the formula (II)

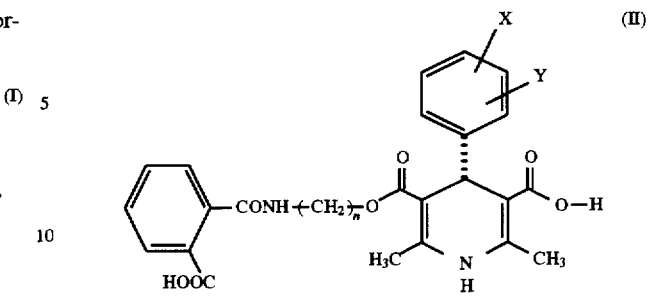

wherein X and Y independently represent a hydrogen atom, a nitro group, a nitrile group or a hydrogen atom; and, n is an integer of 1 to 3 or salts thereof, comprising the step of subjecting a 1,4-dihdropyridine derivative represented by the formula (I)

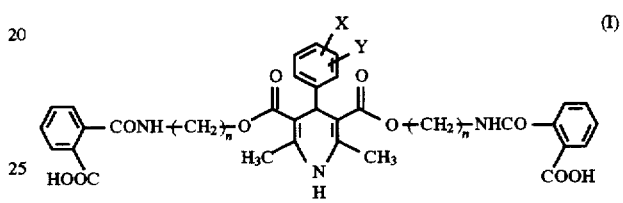

wherein X and Y independently represent a hydrogen atom, a nitro group, a nitrile group or a hydrogen atom; and, n is an integer of 1 to 3 or salts thereof to asymmetric hydrolysis using a microorganism or enzyme.

* * * * *

UNITED STATES PATENT AND TRADEMARK OFFICE
CERTIFICATE OF CORRECTION

PATENT NO. : 5,760,238
DATED : June 2, 1998
INVENTOR(S) : Isshiki, et al.

It is certified that error appears in the above-identified patent and that said Letters Patent is hereby corrected as shown below:

In Column 36, Line 15, "(3-dichlorophenyl)" should be "(3-chlorophenyl)"

On title page of Patent, in Abstract, first line of second paragraph of text, the letter "x" should be upper case, as "X"

Signed and Sealed this

First Day of December, 1998

Attest:

Attesting Officer

BRUCE LEHMAN

Commissioner of Patents and Trademarks